United States Patent
Anderson et al.

(10) Patent No.: US 11,298,564 B2
(45) Date of Patent: Apr. 12, 2022

(54) MEDICAL, SURGICAL AND PATIENT LIGHTING APPARATUS, SYSTEM, METHOD AND CONTROLS WITH PATHOGEN KILLING ELECTROMAGNETIC RADIATION

(71) Applicants: Dennis M. Anderson, Carson City, NV (US); Chelsea A. Doyle, Reno, NV (US); Lynn M. T. Anderson, Carson City, NV (US); Devon E. Anderson, Rochester, NY (US)

(72) Inventors: Dennis M. Anderson, Carson City, NV (US); Chelsea A. Doyle, Reno, NV (US); Lynn M. T. Anderson, Carson City, NV (US); Devon E. Anderson, Rochester, NY (US)

( * ) Notice: Subject to any disclaimer, the term of this patent is extended or adjusted under 35 U.S.C. 154(b) by 0 days.

(21) Appl. No.: 17/062,811

(22) Filed: Oct. 5, 2020

(65) Prior Publication Data
US 2021/0283423 A1    Sep. 16, 2021

Related U.S. Application Data

(60) Provisional application No. 63/003,875, filed on Apr. 1, 2020, provisional application No. 62/987,692, filed on Mar. 10, 2020.

(51) Int. Cl.
*A61N 5/06* (2006.01)

(52) U.S. Cl.
CPC .... *A61N 5/0624* (2013.01); *A61N 2005/0632* (2013.01); *A61N 2005/0644* (2013.01);
(Continued)

(58) Field of Classification Search
CPC .......... A61N 5/0624; A61N 2005/0632; A61N 2005/0644; A61N 2005/0661;
(Continued)

(56) References Cited

U.S. PATENT DOCUMENTS

| 2,215,634 A | 9/1940 | Collins et al. |
| 5,047,072 A | 9/1991 | Wertz et al. |

(Continued)

FOREIGN PATENT DOCUMENTS

| WO | 2008076986 A1 | 6/2008 |
| WO | 2011002209 A2 | 1/2011 |
| WO | 2012122210 A1 | 9/2012 |

OTHER PUBLICATIONS

Buonanno, Manuela, et al. "207-nm UV light—a promising tool for safe low-cost reduction of surgical site infections. I: in vitro studies." PloS one 8.10 (2013): e76968. https://doi.org/10.1371/journal.pone.0076968 (Year: 2013).*

(Continued)

*Primary Examiner* — Jonathan T Kuo
(74) *Attorney, Agent, or Firm* — David Guerra

(57) ABSTRACT

A surgical site infection management lighting system that is effective and safe for human use to reduce or eliminate surgical site infections. The system provides multiple focused electromagnetic radiation frequencies at minimal energy levels for surgical and medical procedures that kills pathogens with electromagnetic radiation sources. The system includes an aiming laser, a distance sensor, a camera for providing images of the surgical site, and a motion sensor for providing control parameters. Fused silica lenses are utilized to focus the visible light for high illumination and selected electromagnetic radiation frequencies at minimal energy levels that are lethal to pathogens. The lighting system can be associated with an articulable arm, a mobile base stand, a handheld unit or a head-mounted unit.

20 Claims, 9 Drawing Sheets

(52) U.S. Cl.
CPC ............... *A61N 2005/0661* (2013.01); *A61N 2005/0662* (2013.01)

(58) Field of Classification Search
CPC ....... A61N 2005/0662; A61N 5/06–2005/073; A61B 18/20–18/28
See application file for complete search history.

(56) References Cited

U.S. PATENT DOCUMENTS

| | | |
|---|---|---|
| 5,072,346 A | 12/1991 | Harding |
| 5,093,769 A | 3/1992 | Luntsford |
| 5,871,522 A | 2/1999 | Sentilles |
| 6,156,503 A | 12/2000 | Drazen et al. |
| 6,461,354 B1 | 10/2002 | Olsen et al. |
| 6,528,306 B1 | 3/2003 | Snyder et al. |
| 6,541,255 B1 | 4/2003 | Snyder et al. |
| 6,573,491 B1 | 6/2003 | Marchitto et al. |
| 6,680,198 B1 | 1/2004 | Snyder et al. |
| 6,724,958 B1 | 4/2004 | German et al. |
| 6,890,346 B2 | 5/2005 | Ganz et al. |
| 7,114,405 B2 | 10/2006 | S?nwoldt et al. |
| 7,677,296 B2 | 3/2010 | Mason |
| 7,776,824 B2 | 8/2010 | Barasch et al. |
| 7,977,110 B2 | 7/2011 | Barasch et al. |
| 8,027,554 B2 | 9/2011 | Takahashi |
| 8,247,376 B2 | 8/2012 | Barasch et al. |
| 8,481,077 B2 | 7/2013 | Kheir et al. |
| 8,531,818 B2 | 9/2013 | Hashimoto et al. |
| 8,817,085 B2 | 8/2014 | Hiltl et al. |
| 9,081,878 B2 | 7/2015 | Rofougaran |
| 9,162,078 B2 | 10/2015 | Irwin |
| 9,220,536 B2 | 12/2015 | Skaggs |
| 9,278,232 B2 | 3/2016 | Gerstenmeier |
| 9,517,280 B2 | 12/2016 | Lynn et al. |
| 9,662,409 B2 | 5/2017 | Rains, Jr. et al. |
| 9,814,906 B2 | 11/2017 | McDaniel |
| 10,010,709 B2 | 7/2018 | Kohane et al. |
| 10,046,175 B2 * | 8/2018 | Gerber ............... A61N 5/0613 |
| 10,064,940 B2 | 9/2018 | Nager |
| 10,483,206 B2 | 11/2019 | Khalid |
| 2007/0045197 A1 * | 3/2007 | Ogut ....................... C02F 1/325 210/748.11 |
| 2008/0183081 A1 * | 7/2008 | Lys ......................... H05B 45/46 600/477 |
| 2010/0234794 A1 | 9/2010 | Weadock et al. |
| 2011/0015492 A1 | 1/2011 | Mangiardi |
| 2011/0054574 A1 | 3/2011 | Felix |
| 2011/0202116 A1 | 8/2011 | Barolet et al. |
| 2012/0206050 A1 * | 8/2012 | Spero ...................... F21K 9/232 315/152 |
| 2013/0274839 A1 * | 10/2013 | Johnson ............... A61N 5/0616 607/90 |
| 2016/0016001 A1 | 1/2016 | Loupis et al. |
| 2016/0082281 A1 * | 3/2016 | Gerber ................ A61N 5/0625 607/94 |
| 2017/0239489 A1 | 8/2017 | Bourke, Jr. et al. |
| 2019/0046812 A1 * | 2/2019 | Harlan ................ A61C 19/004 |
| 2019/0249847 A1 | 8/2019 | Hallack et al. |
| 2019/0255201 A1 | 8/2019 | Rosen et al. |
| 2019/0262629 A1 * | 8/2019 | Broer ................... A61N 5/0621 |
| 2019/0282718 A1 | 9/2019 | Cole |
| 2020/0205268 A1 | 6/2020 | Pereyra et al. |

OTHER PUBLICATIONS

Chandrasekaran, Baskaran, et al. "Short-term multimodal phototherapy approach in a diabetic ulcer patient." Singapore Med J 53.6 (2012): 122-4. (Year: 2012).*

* cited by examiner

MEDICAL, SURGICAL AND PATIENT LIGHTING APPARATUS, SYSTEM, METHOD AND CONTROLS WITH PATHOGEN KILLING ELECTROMAGNETIC RADIATION

CROSS-REFERENCE TO RELATED APPLICATION

This application claims the benefit of priority under 35 U.S.C. § 119(e) based upon U.S. provisional patent application Ser. No. 62/987,692 filed on Mar. 10, 2020, and based upon U.S. provisional patent application Ser. No. 63/003,875 filed on Apr. 1, 2020. The entire disclosures of the prior provisional applications are incorporated herein by reference.

BACKGROUND

Technical Field

The present technology relates to a medical, surgical and/or patient lighting apparatus, system, method and controls for use in connection with providing surgical or patient care lighting utilizing multiple wavelengths and bandwidths of pathogen killing electromagnet radiation frequencies and/or visible and ultraviolet light.

Background Description

Certain wavelengths in both ultraviolet and visible light have germicidal and bactericidal benefits for medical applications. To date, the medical industry does not use germicidal and bactericidal visible light or ultraviolet light during surgical procedures to manage surgical site infections. However, a limited application of ultraviolet light for bactericidal controls are practiced in dental medicine with small and focused emitting handheld equipment for sterilization of root canal and dental implants. The present technology uses a novel application of multiple frequencies, wavelength bandwidths of ultraviolet and visible light during surgical and medical procedures. In 2017, a group from Loyola University reported that in the United States annually, surgical site infections range between 160,000 and 300,000 at a cost of $3.5 to $10 Billion. These costs are related to additional time and care provided to the patients as hospital times are extended to treat surgical site infections. In addition to the high cost and the emotional and physical setbacks that patients suffer from acquiring a surgical site infection, it is documented that about 8,200 Americans die each year from infections caused during surgery. This pervasive problem is addressed herein with programmable lights and electromagnet radiation methods using an apparatus to kill bacteria, viruses, and pathogens in real time during surgical procedures. Various ultraviolet radiations contain wavelengths that can be carcinogenic with over exposure. In the present technology, health risks of over exposures are managed through timed or cycled radiation to administer energy levels within a safe and effective time frame and light frequency range. When electromagnet radiation is managed both for energy levels and exposure times, the use of electromagnet radiation, along with some visible light wavelengths, can kill bacteria viruses and pathogens and be safe of human exposure.

In addition to the surgical light systems light providing illumination and bactericidal benefits, the present technology is designed to use man-made ultraviolet radiation with a wavelength between 300 and 310 nm, at a safe dose rate and scheduled protocol, such that the patient's skin will synthesize vitamin D and D3 to further promote biologic healing at the surgical site.

In 2013, Buonanno, et al. reported 207-nanometer ultraviolet light as a bactericidal tool for surgical site infections. The research indicated that the 207-nanometer ultraviolet light is both safe and beneficial for humans during surgical procedures. Their conclusions were that the 207-nanometer ultraviolet light could be safe and cost effective for surgical site infection management.

Recent work by Yamono et al. (2020) indicates that direct and repetitive illumination from 222-nm ultraviolet radiation C (UVC), which is a powerful sterilizer, does not cause skin cancer in an animal model. The research also suggests that 222-nm UVC is safe for human eyes and skin. The ultraviolet radiation of 222 nanometers has similar antimicrobial effects compared with radiation of 254 nanometers that is known to have human health risks and is considered to be carcinogenic.

Visible light is used in the present technology and provides both illumination and bactericidal effects. Blue light in the spectral range of 407 to 470 nanometers (frequency (749-599 terahertz) is known to kill various pathogens. Other visible light wavelength bandwidths in the 488 to 514 nanometer (frequencies 614-583 terahertz) range also kills various bacteria and higher bandwidths around 630 or 780 nanometers (frequencies 475-384 terahertz) are also utilized to kill certain bacteria, viruses and pathogens during application in the medical and dental practice. Each wavelength in both the ultraviolet range and the visible light range are combined into a lighting and radiation system that is programmed to be safe for human use and provide bactericidal functions.

Additional ultraviolet and visible lights are known to kill airborne microbial diseases.

While the above-described devices fulfill their respective, particular objectives and requirements, the aforementioned devices or systems do not describe a medical lighting apparatus, system, method and controls that utilize a 200 to 222 nanometer wavelength as one of many ultraviolet wavelengths integrated into a programmable lighting system for managing or killing surface and airborne pathogens or diseases in medical use during surgery or dental procedures.

A need exists for a new and novel medical lighting apparatus, system, method and controls that can be used for managing or killing surface and airborne pathogens or diseases in medical use during surgery or dental procedures. In this regard, the present technology substantially fulfills this need. In this respect, the medical lighting apparatus, system, method and controls according to the present technology substantially departs from the conventional concepts and designs of the prior art with the use of a fully integrated lighting and pathogen destruction electromagnet radiation system. In doing so provides an apparatus primarily developed for the purpose of managing or killing surface and airborne pathogens or diseases in medical use during surgery or dental procedures.

SUMMARY

In view of the foregoing disadvantages inherent in the known types of pathogen killing light systems, the present technology provides a novel medical lighting apparatus, system, method and controls, and overcomes one or more of the mentioned disadvantages and drawbacks of the prior art. As such, the general purpose of the present technology, which will be described subsequently in greater detail, is to provide a new and novel medical lighting apparatus, system, method and controls and method which has all the advantages of the prior art mentioned heretofore and many novel features that result in a medical lighting apparatus, system, method and controls which is not anticipated, rendered obvious, suggested, or even implied by the prior art, either alone or in any combination thereof.

According to one aspect of the present technology, there can be provided an electromagnetic radiation system for providing bactericidal, germicidal, antimicrobial and/or pathogen killing effects. The electromagnetic radiation system can include a first electromagnetic radiation source, a second electromagnetic radiation source and a third light source. The first electromagnetic radiation source can be configured to radiate a first electromagnetic radiation at a frequency selected from the group consisting of 1.489-1.350 petahertz (PHz), and 999-967 terahertz (THz). The second electromagnetic radiation source can be configured to radiate a second electromagnetic radiation at a frequency selected from the group consisting of 749-637 THz, 614-583 THz, and 475-384 THz. The third light source can be configured to radiate visible light at a wavelength, bandwidth or frequency different to that of the second electromagnetic radiation. The third light source function is to provide illuminating an area for high visibility and is for the benefit of the surgeon and medical staff that are performing a surgical or medical procedure on the patient. The first and second electromagnetic radiation frequencies can be configured or configurable to deliver human safe electromagnetic radiation doses to site specific infections on a patient that is effective in destroying harmful pathogens. An energy level of the first electromagnetic radiation and the second electromagnetic radiation is power in watts multiplied by the dose time in seconds. The pathogen killing electromagnet radiation dose can be configured or configurable for delivery to each square centimeter of a surgical or medical procedure target site on the patient.

According to another aspect of the present technology, there can be provided a method of using an electromagnetic radiation system for providing bactericidal, germicidal, antimicrobial and/or pathogen killing effects to a patient or animal care. The method can include the steps of providing a first electromagnetic radiation source, a second electromagnetic radiation source and a third light source. The method can include providing an electromagnetic radiation system deployable using an attachable device selected from the group consisting of an articulable arm, a floor stand, a mobile base, and a handheld unit. The electromagnetic radiation system can include a first electromagnetic radiation source, a second electromagnetic radiation source and a third light source. The third light source can be configured or configurable to provide illumination for visibility of a first area of a patient, which is the entire patient and much of the surgery room. Additional illuminating for high visibility of the surgical site is also provided from the third light source by using lenses to focus the third light source. The first electromagnetic radiation and the second electromagnetic radiation of the surgical site provides for pathogen destruction in the surgical site area. The surgical or medical procedure site target area can have a size less than and within the first area. Providing bactericidal, germicidal, antimicrobial and/or pathogen killing effects to the surgical or medical procedure target area by controlling a parameter of any one or any combination of the first electromagnetic radiation source and the second electromagnetic radiation source. The parameter can be selected from the group consisting of intensity, electromagnetic radiation time, and a distance between the electromagnetic radiation system and the target area. The first electromagnetic radiation source and the second electromagnetic radiation source can be configured or configurable to deliver human safe and pathogen killing electromagnetic radiation at a predetermined dose to the surgical or medical procedures target area.

According to yet another aspect of the present technology, there can be provided a programmable electromagnetic radiation system utilizable in a head lamp for providing bactericidal, germicidal, antimicrobial and/or pathogen killing effects to a target site on a patient. The electromagnetic radiation system can include a first electromagnetic radiation source, a second electromagnetic radiation source, a third light source, a computer system and a head lamp assembly. The first electromagnetic radiation source can be configured to radiate a first electromagnetic radiation at a frequency selected from the group consisting of 1.489-1.350 PHz, and 999-967 THz. The second electromagnetic radiation source can be configured to radiate a second electromagnetic radiation at a frequency selected from the group consisting of 749-637 THz, 614-583 THz, and 475-384 THz. The third light source can be configured to radiate visible light at a wavelength, bandwidth or frequency different to that of the second electromagnetic radiation. The third light source can be configured or configurable to provide illumination for visibility of a target site on the patient. The computer system can be configured or configurable to control any one or any combination of the first electromagnetic radiation source, the second electromagnetic radiation source, and the third light source to deliver human safe pathogen killing electromagnetic radiation at a predetermined energy level and dose time to reduce or eliminate site specific infections at the target site on the patient. The head lamp assembly can be configured to include the first electromagnetic radiation source, the second electromagnetic radiation source, and the third light source. An energy level of the first electromagnetic radiation and the second electromagnetic radiation is power in watts multiplied by the dose time in seconds. The energy level can be configured or configurable for delivery to each square centimeter of the target site on the patient.

According to still another aspect of the present technology, there can be provided a lighting system for providing bactericidal, germicidal, antimicrobial and/or pathogen killing effects to a target site on a patient. The light system can include a first light source configured to radiate ultraviolet light at a wavelength selected from the group consisting of 200-222 nanometers (nm) with frequencies of 1.489-1.350 PHz and 300-310 nm with frequencies of 999-967 THz. A second light source configured to radiate a first visible light at a wavelength selected from the group consisting of 400-470 nm with frequencies of 749-637 THz, 488-514 nm with frequencies of 614-583 THz, and 630-780 nm with frequencies 475-384 THz. The pathogen killing aspects of the first and the second electromagnetic radiation are the frequency and the energy thereof. An energy required to kill selected pathogens is a power in watts that delivers the electromagnetic radiation frequency to the target site multiplied by a time in seconds. This level of radiation is lethal to the pathogen and harmless to human cells and the patient. A third light source can be configured to radiate visible light configured to radiate a third visible light not at the wavelength of the first visible light. Electrical engineering, mechanical engineering, biomedical engineering, and computer programming are used to ensure the correct energy level and dose time are designed and employed to delivered human safe pathogen killing electromagnetic radiation to reduce or eliminate surgical site infections for patients that are undergoing surgical or medical procedures In some or all embodiments of the present technology, the first electromagnetic radiation source can be a plurality of first electromagnetic radiation sources with one or more of the first electromagnetic radiation sources including a focusable lens and one or more not including the focusable lens. The second electromagnetic radiation source can be a plurality of second electromagnetic radiation sources with one or more of the second electromagnetic radiation sources including the focusable lens and one or more of the second electromagnetic radiation sources not including the focusable lens.

In some or all embodiments of the present technology, the third light source can be configured or configurable to provide illumination for visibility of the target site and includes focusable lenses.

Any or all embodiments of the present technology can include a laser unit located centrally within an array of the first electromagnetic radiation source, the second electromagnetic radiation source and the third light source. The laser unit can be configured to radiate laser light toward an illumination area illuminated by the first light source, the second light source.

Any or all embodiments of the present technology can include a distance sensor configured to sense reflected laser light utilizable in determining a distance of the first electromagnetic radiation source, the second electromagnetic radiation source and the third light source to the target site.

Any or all embodiments of the present technology can include a camera configured to capture an image or video of at least the target site.

Any or all embodiments of the present technology can include a motion sensor configured to detect motion in an area above the target site or adjacent the first electromagnetic radiation source, the second electromagnetic radiation source.

Any or all embodiments of the present technology can include a computer system in operable communication with any one or any combination of the first electromagnetic radiation source, the second electromagnetic radiation source, the third light source, a laser unit, a distance sensor, a camera, and a motion sensor.

In some or all embodiments of the present technology, the computer system can be configured or configurable to control any one or any combination of the first electromagnetic radiation source, the second electromagnetic radiation source and the third light source, and configured or configurable to receive signals from the distance sensor and the motion sensor.

In some or all embodiments of the present technology, the first electromagnetic radiation source, the second electromagnetic radiation source and the third light source can be integrated in a body.

In some or all embodiments of the present technology, the body can be attachable to a device selected from the group consisting of an articulable arm, a floor stand, a mobile base, and a handheld unit.

Any or all embodiments of the present technology can include a signage configured to illuminate when any one or any combination of the first electromagnetic radiation source and the second electromagnetic radiation source is active.

In some or all embodiments of the present technology, the second electromagnetic radiation source can be configured to radiate in the frequency range of 749-599 THz.

In some or all embodiments of the present technology, the first electromagnetic radiation source and the second electromagnetic radiation source can be configured or configurable to radiate the first electromagnetic radiation and the second electromagnetic radiation, respectively, to an area larger than a largest width of the surgical or medical procedures target site.

In some or all embodiments of the present technology, the first electromagnetic radiation frequency and the energy level thereof can be configured to provide a radiation level sufficient to kill a set of selected pathogens and to be harmless to the patient.

Any or all embodiments of the present technology can include an aiming light from a laser unit positioned in a center of an array of the first electromagnetic radiation source, the second electromagnetic radiation source and the third light source.

Any or all embodiments of the present technology can include determining the distance between the electromagnetic radiation system and the target area by a distance sensor configured to sense reflected laser light emitting from a laser unit. Where the measured distance to target area and area of electromagnetic radiation in square centimeters at the target site are used to set the power level for the radiation to the minimum pathogen killing effects of the radiation at the surgical or medical procedures site so that excess radiation of the target area does not occur.

Any or all embodiments of the present technology can include controlling any one or any combination of the first electromagnetic radiation source and the second electromagnetic radiation source by any one or any combination of a computer system in operable communication therewith and a motion sensor.

Any or all embodiments of the present technology can include displaying to a display an image or video of an illumination area captured by a camera.

Any or all embodiments of the present technology can include where a distance information between the electromagnetic radiation system and the target site is used to automatically or manually adjust a focus and an intensity of the visible and electromagnetic radiation to deliver effective doses sufficient to kill pathogens while ensuring no harmful effects on cells in the target site and no harmful effects to the patient, and where a visible laser is configured to measure the distance from the electromagnetic radiation system to the target site, and to show a center of the first and second electromagnetic radiation on the target set focused by a lens.

There has thus been outlined, rather broadly, features of the present technology in order that the detailed description thereof that follows may be better understood and in order that the present contribution to the art may be better appreciated.

Numerous objectives, features and advantages of the present technology will be readily apparent to those of ordinary skill in the art upon a reading of the following detailed description of the present technology, but nonetheless illustrative, embodiments of the present technology when taken in conjunction with the accompanying drawings.

As such, those skilled in the art will appreciate that the conception, upon which this disclosure is based, may readily be utilized as a basis for the designing of other structures, methods and systems for carrying out the several purposes of the present technology. It is, therefore, that the claims be regarded as including such equivalent constructions insofar as they do not depart from the spirit and scope of the present technology.

It is therefore an objective of the present technology to provide a new and novel medical lighting apparatus, system, method and controls that has all of the advantages of the prior art pathogen killing light systems and none of the disadvantages.

It is another objective of the present technology to provide a new and novel medical lighting apparatus, system, method and controls that may be easily and efficiently manufactured and marketed.

An even further objective of the present technology is to provide a new and novel medical lighting apparatus, system, method and controls that has a low cost of manufacture with regard to both materials and labor, and which accordingly will become available for sale at affordable for to the medical industry. Thereby making such medical lighting apparatus, system, method and controls economically available to the buying public.

Still another objective of the present technology is to provide a new medical lighting apparatus, system, method and controls that provides in the apparatuses and methods of the prior art some of the advantages thereof, while simultaneously overcoming some of the disadvantages normally associated therewith.

These together with other objectives of the present technology, along with the various features of novelty that characterize the present technology, are pointed out with particularity in the claims annexed to and forming a part of this disclosure. For a better understanding of the present technology, its operating advantages and the specific objectives attained by its uses, reference should be made to the accompanying drawings and descriptive matter in which there are illustrated embodiments of the present technology. Whilst multiple objectives of the present technology have been identified herein, it will be understood that the claimed present technology is not limited to meeting most or all of the objectives identified and that some embodiments of the present technology may meet only one such objective or none at all.

BRIEF DESCRIPTION OF THE DRAWINGS

The present technology will be better understood and objectives other than those set forth above will become apparent when consideration is given to the following detailed description thereof. Such description makes reference to the annexed drawings wherein.

The same reference numerals refer to the same parts throughout the various figures.

DETAILED DESCRIPTION OF THE EMBODIMENTS

Figure 1:
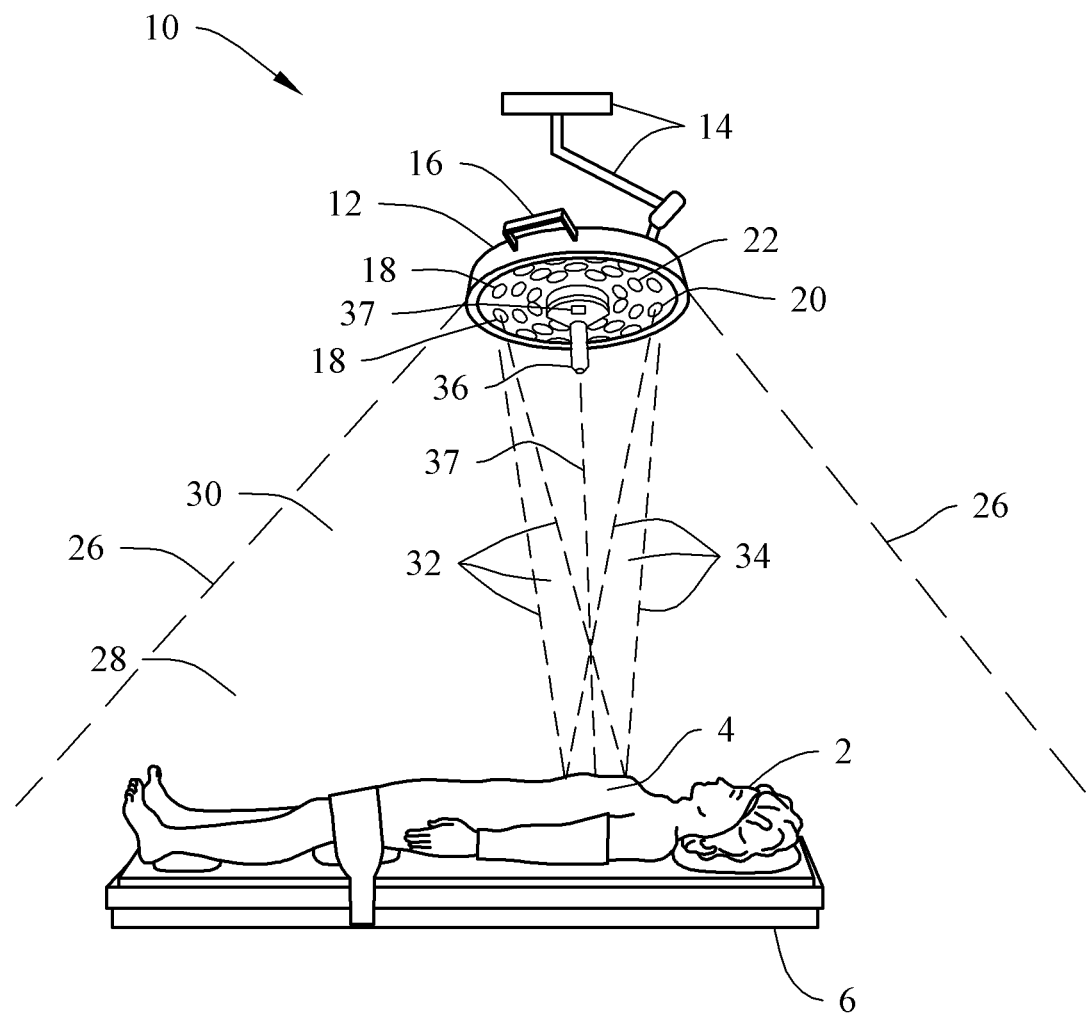
FIG. 1 is a perspective view of an embodiment of the medical lighting apparatus, system, method and controls constructed in accordance with the principles of the present technology.

In the following description, for purposes of explanation and not limitation, specific details are set forth, such as particular embodiments, procedures, techniques, etc. to provide a thorough understanding of the present technology. However, it will be apparent to one skilled in the art that the present technology may be practiced in other embodiments that depart from these specific details.

Frequencies at a designed and employed energy level in both ultraviolet and visible light have germicidal and bactericidal benefits for medical applications. The present technology is novel because it provides multiple frequencies-, wavelengths or bandwidths of ultraviolet and visible light for illumination and pathogen killing electromagnetic radiation are all part of the integrated lighting system that are used during a medical procedure or surgery. The apparatus is designed for use as a safe bactericidal system using electromagnetic radiation in selected frequencies on a programmed scheduled energy and timed dose that uses a method and apparatus for optimal health benefits. Furthermore, it reduces the risk of surgical site infection for the patient. The multiple electromagnetic radiation frequencies and bandwidths are controlled separately through computer programming to provide safe and effective timed dose of the specific electromagnetic radiation with selected frequencies at a programmed or set energy level. The control programming may be cycled on and off over a time period to optimize the health benefits and minimize harmful effects of radiation. The present technology has the capacity for use in real time during a surgical or wound care procedure to reduce surgical site infections by using several spectrums of visible and ultraviolet light and their associated frequency ranges to kill pathogens and microorganisms.

In addition to use during surgical or emergency medical procedures, the apparatus and methods have an equal value for patient care in postoperative patient care. The combined use of the invention during real time surgical procedures and during follow-up care has potential to reduce surgical and wound infections. Surgical site infections prolong the patient's hospital stay on an average of over nine days which substantially increases the cost of patient care.

The present technology may also include the health benefits related to pre-vitamin D synthesis from ultraviolet radiation. The present technology is designed to promote healing by using the medium wavelength ultraviolet radiation as a growth stimulus for cells, tissues, and bones in animals, specifically, humans. The invention uses a combination of light emitting diodes (LED) and specialized gas vapor bulbs as a medical tool and treatment to produce a wavelength of the radiation is within the ultraviolet range of 300 to 310 nanometers. This radiation range is equivalent to the ultraviolet-B sunlight and is responsible for production of vitamin D in the human skin. Vitamin D is vital to life and has been associated with many health benefits.

Light skinned humans adsorb ultraviolet-B sunlight at a rate approximately five times faster than dark skinned humans. Skin color is a factor in treatment when using 300 to 310 nanometers ultraviolet radiations that is generated by specialized lighting equipment and bulbs. This frequency range of 999 to 967 THz at the correct dose will not damage or kill cells as the energy level and time of exposure is programmed and controlled to be safe and healthy.

The apparatus, methods and controls that are used in surgical lighting also provide real time safe bactericidal advantages over lighting that only provides illumination. The present technology is novel over surgical lighting by providing multiple wavelengths or multiple bandwidths of visible light for constant illumination of the surgical field as well as programmable electromagnetic radiation at human safe energy levels to deliver focused and managed doses of bactericidal radiation during a medical or surgical procedure and postoperative patient care. The surgical and patient care lighting system operates with exposure levels that are harmless to humans and lethal to harmful pathogens that cause infection and retard healing. The programmable light and electromagnetic radiation doses, i.e. energy level and time of exposure, are delivered on a scheduled basis, typically three or more short dose exposures of 1.448 PHz frequency for a surgical procedure or for entirely harmless pathogen killing electromagnetic radiation, that would be delivered to the target area on a scheduled dose, or blue light in the spectral range of 749 to 637 THz that can have scheduled doses or can remain on safely throughout the surgical procedure. The dose to kill bacteria, viruses, microbes, or parasites may range from less than a second and, typically, up to several seconds which is delivered pre-, intra- and post-operatively. This safe bactericidal practice uses electromagnetic radiation on a scheduled energy and timed dose in a method and apparatus for optimal health benefits and reduction or potential elimination of surgical site infection for the patient. The electromagnetic radiation frequencies that are used during the medical procedure and the dose of the electromagnetic radiation are managed to be harmless to the patient and lethal to bacteria, viruses, and parasites. The delivery of the pathogen killing lighting is achieved by focusing the bean of radiation through a fused silica lens. These lenses will need to meet the specifications and objectives of a pathogen killing overhead surgical light system. The specific fused silica lenses that are commercially available may not meet the special design criteria for use in the present technology. However, the technology to build these lenses exists and commercial lens companies can be contracted for specialty lens production. The design specifications for the surgical lighting system will be based on delivery of electromagnetic radiation as a selected dose to the target area surgical site from an overhead or portable lighting equipment. For example if the overhead lighting system is 180 centimeters above the patient's surgical site, the focusing lens may be employed to project 20 millijoules over a ten second period of electromagnetic radiation with frequencies 1.489-1.350 PHz, and 999-967 Hz. in an area of a circle that is 20 centimeters (an area of 314 square centimeters). The energy level of the electromagnetic radiation is engineered, scheduled and programmed to meet the pathogen killing objectives and be entirely harmless to the patient, surgeon and medical staff.

Buonanno et al. (2013) previously reported 207 nanometer ultraviolet light as a bactericidal tool for surgical site infections. The research indicated that the 207-nanometers ultraviolet light (electromagnetic radiations with a frequency of 1.448 PHz) is both safe and beneficial for humans during surgical procedures.

Buonanno et al. (2017) published a follow-up study that presented the used ultraviolet C light in the range of 200 to 222-nanometers. The researchers selected the UVC light because of its limited penetration distance into biological samples and are basically lethal effect on several bacteria but do not damage cells or tissue. The 200 to 222-nanometer UVC wavelength has a similar cidal effect on pathogens to a 254-nanometer wavelength UVC light. UVC light with 254-nanometes is known to kill around 60 pathogens with does from a fraction of a second to just over nine minutes, however the 254-nanometer light is not safe for human exposure and is therefore typically used in bactericidal application that are enclosed and not available for human exposure, such as enclosed heating and air-condition systems.

The wavelength of the visible or ultraviolet light, such as 200 nanometers, is a dimensional description of the peak to peak sinusoidal wavelength that is emitted by solar energy or manmade equipment. The photon energy (eV, aJ) is an additional criteria used for electrical engineering system for a given visible or ultraviolet light. An electron-volt (symbol eV) is the amount of kinetic energy gained by a single electron accelerating from rest through an electric potential difference of one volt in vacuum, and aJ is an energy expression where one attojoule=$10^{-18}$ joules.

For example, ultraviolet C light with wavelengths between 100 and 208 nanometers has photon energy of 4.43 to 12.4 electron volt (eV): 0.701 tp 1.987 aJ. In addition, the visible and ultraviolet light has a frequency that utilizes the energy through vibration at a certain cycle, such as 200 to 222 nanometer ultraviolet radiation has a frequency between 1.489 and 1.350 PHz. These are significant criteria when calculating the pathogen destruction engineering and design for a surgical or medical procedures light system. With respect the biological criteria and the biomedical and biomedical-engineering design of the pathogen killing visible and ultraviolet surgical and medical procedures lighting system utilizes the relative size difference of a human cell that is typically 10 microns. In contrast harmful pathogens such as bacteria are typically less than one micron and viruses are in the size range around 100 nanometers. So human cells, that need to be protected and preserved are in general 10 to 100 time larger and unaffected by the design dose of selected electromagnetic radiation light that kills the harmful pathogens that are targeted by the lighting system in the present invention. In conclusion, the frequency vibration and the energy applied by the selected electromagnetic radiation with frequencies 1.489-1.350 PHz and/or 999-967 THz in the ultraviolet spectrum and with frequencies 749-637 THz, 614-583 THz, and 475-384 THz in the visible light spectrum for pathogen destruction kills the pathogens are harmless to human cells that are typically one or more magnitudes larger than pathogens. Hence, electrical, mechanical, and biomedical engineering as applied to the apparatus, systems, methods, and computer controls affords the present invention novel status. By knowing the targeted pathogen population and destruction criteria, the lighting system design and manufacturing, as used in a surgical or medical procedures setting, can safely achieve scheduled pathogen destruction with doses of effective energy and time periods while preserving healthy human cells and optimum patient health. The present invention, in a non-obvious manner, employs multiple disciplines of engineering, science, and design to invent a novel integrated surgical and medical procedure lighting system that is effective for pathogen destruction and safe for human use to reduce or eliminate surgical site infections.

The present technology uses light for illumination in combination with programmable electromagnetic radiation frequencies that provide scheduled doses of the various frequencies both for energy levels and timed exposure for safe use and concurrent health benefits. Considerations for individual patients based on their skin coloration and tone can be programmed into the lighting and radiation system to safe exposure levels at an optimum dose. The Fitzpatrick skin table that uses six categories for color from 1 very light skin to 6 very dark skin may be used when programming the lighting and radiation equipment to ensure safety for all persons exposed to the equipment light and radiation. A motion detector in the lighting system will turn off all wavelengths that could be harmful to humans or animals.

The visible light that is used in the present technology provides both illumination and bactericidal benefits. Blue light in the spectral range of 407 to 470-nanometers with a frequency range of 749 to 637 THz is known to kill at least 26 known pathogens such as gram-positive *Streptococcus thermophiles* and methicillin resistant *Staphylococcus aureus* (MRSA), which relates to a cost of 2.3 to 4.2 billion dollars per year as hospital expenses for the MRSA infection management.

Ultraviolet light at 207-nanometer (frequency 1.448 PHz) will be safe and cost effective as a supplemental tool for surgical site infection prevention, in addition to per-operative antibiotic use. The 207-nanometer wavelength is one of the ultraviolet wavelengths that is utilized it the present invention's programmable lighting system for medical use during surgery or dental practice to manage surgical site infection with the use of germicidal, bactericidal, and virus control of harmful microbes. The present technology uses light for illumination in combination with programmable electromagnetic radiation frequencies at selected energy levels to provide scheduled doses of the pathogen killing radiation with energy levels and timed exposure for safe use with multiple healthy benefits.

Selected electromagnetic radiation as used as used in the present invention during intra-operative and post-operative care can kill bacteria, protozoa, viruses, and yeast in relatively short periods of time, typically measured in seconds. The electromagnetic radiation frequencies, energy level, and time of exposure are assessed to be effective in destruction of harmful agents, while also being managed to be harmless to patient. Microorganisms quickly absorb ultraviolet—C radiation which destroys the microbe's DNA, typically in time periods that are insignificant to human health. Some microbes are killed in less than one second, while other forms of bacteria, protozoa and viruses can take up to several minutes to kill depending on the frequency and dose of electromagnetic radiation. The present technology's primary function and purpose is the care, health, and wellbeing of each patient. As such, apparatus, methods, and electronic controls used in the invention limit adverse effects to a patient by limiting the dose of visible and ultraviolet light radiation along with a factor of safety to ensure no harmful impact to a patient's tissues or organs that benefit from the death and destruction of harmful pathogens.

The use of the spectrum of radiation of visible and ultraviolet light as generated by the sun available for use in the present invention lighting system that is managed by the computer-controlled method, apparatus, and system to provide safe and effective health benefits for humans and other applications. The method, apparatus, and system may include use without human exposure for bactericidal, germicidal, virus and pathogen destruction in vacant rooms as a pre-operative sterilization method. A motion detection sensor will allow the system to shut off or reduce the light and radiation for safe and beneficial human exposures of the various wavelengths.

The present technology is intended for focused application of selected electromagnetic radiation frequencies for use within surgical fields as a bactericidal and germicidal system that reduces or eliminates surgical site infections. The lighting system may also provide ultraviolet A light in controlled doses for the synthesis of pre-vitamin D in human skin for optimal health.

Referring now to the drawings, and particularly to FIGS. 1-10, an embodiment of the medical lighting apparatus, system, method and controls of the present technology is shown and generally designated by the reference numeral 10.

Figure 2:
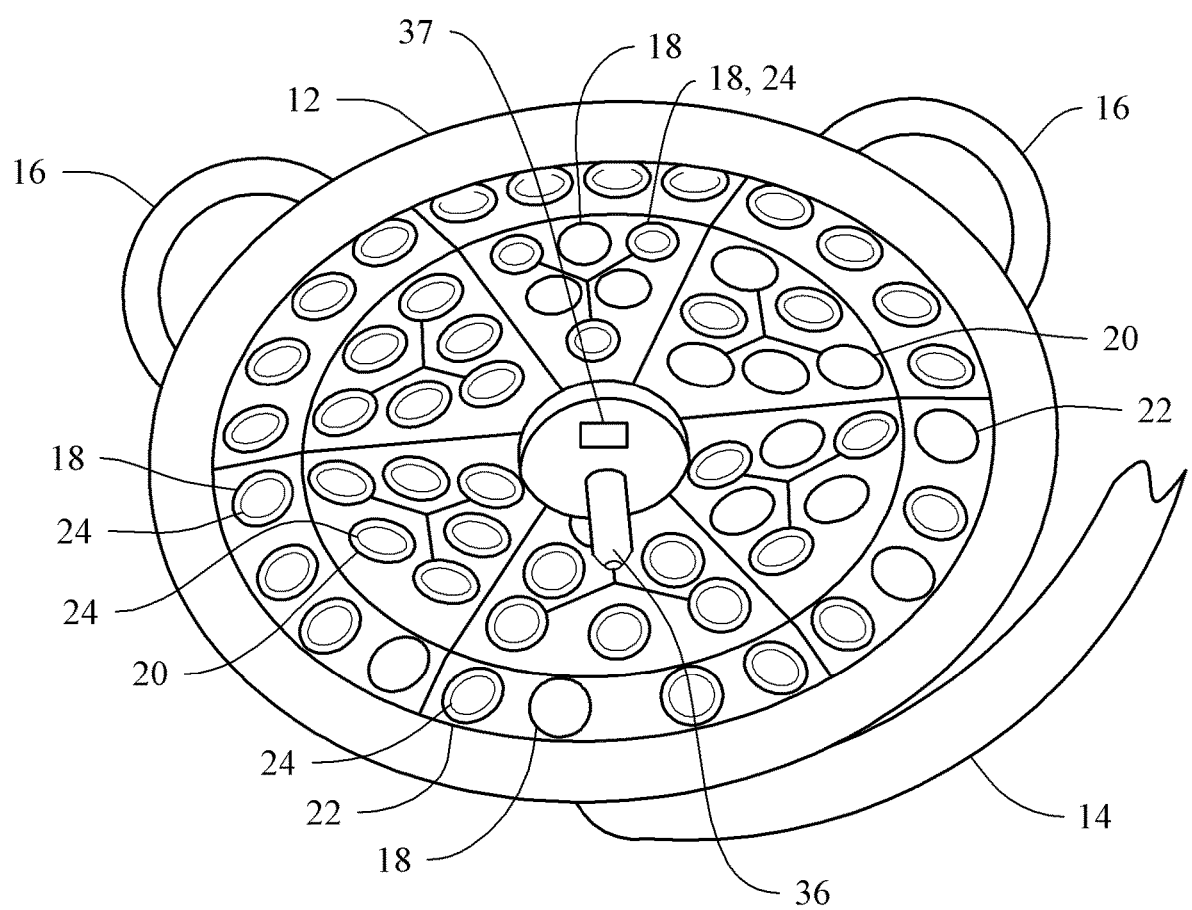
FIG. 2 is an enlarged perspective view of the medical lighting apparatus of the present technology.

Referring to FIGS. 1 and 2, a new and novel medical lighting and electromagnetic radiation apparatus, system, method and controls 10 of the present technology for managing or killing airborne pathogens or diseases in medical use during surgery or dental procedures is illustrated and will be described. More particularly, the medical lighting apparatus and system 10 can be a stationary apparatus containing multiple visible light sources and multiple electromagnetic radiation sources that produce illumination of surgical or medical procedure sites and provide bactericidal and germicidal effects, where each of the various light and radiation sources are controlled separately to provide a timed dose at either a set energy level or a variable energy level. Every light in the fixture can be programmed to project a light source for a surgical site or medical procedures illumination, for human safe pathogen killing visible light, and/or for human safe pathogen killing electromagnetic radiation. The first electromagnetic radiation sources have selected frequencies of 1.489-1.350 PHz, and frequencies 999-967 THz. The second electromagnetic radiation sources have selected frequencies of 749-637 THz, 614-583 THz, and 475-384 THz et cetera can all be within the suite of lights and radiation within the surgical site infection lighting system. The programmable lighting and electromagnetic radiation system can used fused silica lens to focus the pathogen killing beams on the active surgical site. The system also has a visible laser that is used to ensure that the pathogen killing visible and ultraviolet radiation sources are focused on illuminating the specific zone where the surgical procedure is being performed.

The present technology can include a light fixture or housing 12 that support multiple lights or lamps in a variety of patterns or arrays. The lights can provide a myriad of visible and ultraviolet, frequencies, wavelengths or bandwidths of lighting to provide illumination for surgical procedures and bactericidal, germicidal, and antimicrobial radiation during surgical procedures. The housing 12 can be supported by an adjustable or articulating mounting arm 14 to secure the lighting fixture for solid and safe use. The mounting arm 14 can be secured to a wall, ceiling or any mountable structure. Further the mounting arm 14 can include a conduit for power cords and computer control wiring. It can be appreciated that a motor and gearing assembly (not shown) can be utilized to move the housing 12 and/or the mounting 14.

The housing 12 can include a manual handle 16 for positioning the light fixture in a variety of orientations, angles, and/or locations. It can be appreciated that the handle 16 can take many shapes and configurations.

The housing 12 can be positioned above a patient 2 supported on a table 6 or the like so that a treatment or surgical site 4 is facing in a general direction of the present technology. The handle 16 can be utilized to position the housing 12 so as to direct light radiating therefrom toward the surgical site 4.

The array of lights associated with the housing 12 can be the second electromagnetic radiation sources which have selected frequencies of 749-637 THz, 614-583 THz, and 475-384 THz 18, the first electromagnetic radiation sources have selected frequencies of 1.489-1.350 PHz, and frequencies 999-967 THz 20 and the third light source to provide for illuminating an area for high visibility and is for the benefit of the surgeon and medical staff that are performing a surgical or medical procedure on the patient with multiple highly illuminating light sources such as but not limited to light emitting diodes (LEDs) 22. Fused silica lenses 24 can be utilized with any one or combination of the second electromagnetic radiation 18, the first electromagnetic radiation units 20 and/or third light sources to provide illuminating an area with LEDs and other high luminescence lighting 22. The silica lenses 24 can be configured to focus the pathogen killing beams of visible and ultraviolet overhead lighting on the active surgical site 4. It can be appreciated that the array of lights can include a combination of some of the second and first electromagnetic radiations 18, 20, 22 with the silica lenses 24 and some without.

The second electromagnetic radiation 18 and the first electromagnetic radiation units 20 can be configured to radiate light that has bactericidal, germicidal, and antimicrobial radiation benefits. The exposure level and amount of time of exposure can be controlled and/or engineered to be safe for humans. These focused beams of the second electromagnetic radiation 18 may be turned on and off multiple times during an operation or medical procedure.

The LEDs 22 can be configured to provide high visibility for surgeons and medical staff during an operation or medical procedure.

The pathogen killing electromagnetic radiation sources and the lights for illumination 18, 20, 22 provide an effective area of all light and radiation illumination 26. The second electromagnetic radiation—18 can be focused to radiate an area 28 where visible light is used for bactericidal, germicidal, and antimicrobial radiation that is 100% safe for human exposure, including the patient 2 and medical staff at any exposure level and amount of time. Additionally, the second electromagnetic radiation 18 can be focused to a target or concentration area 32 on a specific site, such as the surgical site 4. This can be accomplished by adjusting the silica lens 24 associated with any combination of the second electromagnetic radiation 18.

The first electromagnetic radiation units 20 can be focused to radiate an area 30 where ultraviolet light is used for bactericidal, germicidal, and antimicrobial radiation that is 100% safe for human exposure, including the patient 2 and medical staff. Additionally, the first electromagnetic radiation units 20 can be focused to a target or concentration area 34 on a specific site, such as the surgical site 4. This can be accomplished by adjusting the silica lens 24 associated with any combination of the first electromagnetic radiation units 20.

The present technology 10 can further include a laser unit 36 can is configured to project a safe colored laser beam 38 that shows the area where the focused bactericidal, germicidal, and antimicrobial radiation from the second electromagnetic radiation 18 and invisible first electromagnetic radiation units 20 are being directed. This laser beam 38 will only be visible during time of radiation and allows medical staff to ensure that the bactericidal, germicidal, and antimicrobial radiation is radiating the surgical site 4. The laser unit 36 can be configured or aimed to show a center of the safe pathogen killing lighting. The laser unit 36 can include a distance sensor 39 have the capability of measuring the precise distance between the pathogen killing electromagnetic radiation sources and the lights for illumination 18, 20, 22 and/or housing 12 and the surgical site 4, and can be used as part of the control systems to set the engineering energy level and time of the electromagnetic radiation dose from the second electromagnetic radiation 18 and first electromagnetic radiation units 20. Also, within the center of the lighting system there can be a camera 37 with an adjustable lens for magnification to observe a surgical or medical procedure in real time and can be used to record the procedure for later viewing.

Figure 3:
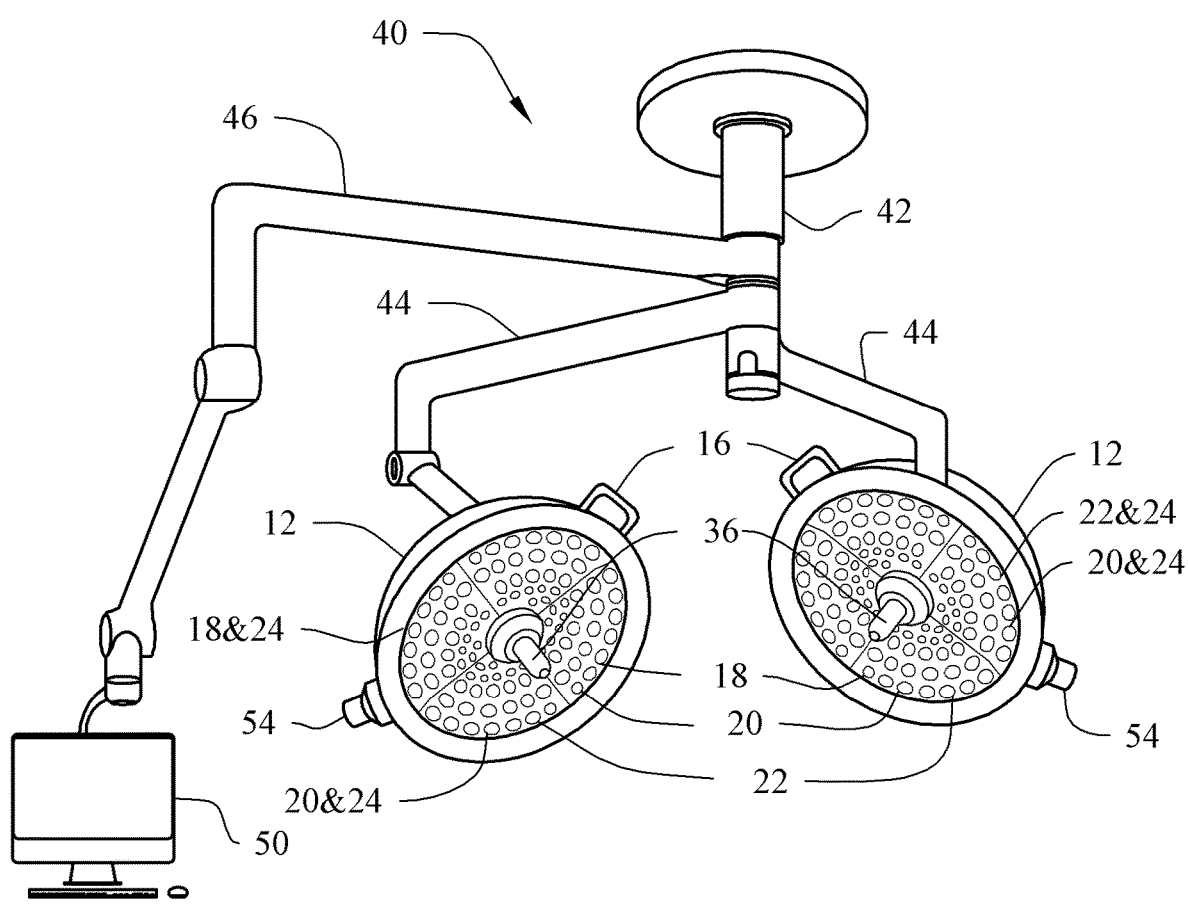
FIG. 3 is a perspective view of the dual embodiment of the present technology.

Referring to FIG. 3, an articulated system 40 of the present technology can be utilized which include a wall or ceiling mounting structure 42 with an extended shaft platform. Multiple articulating arms 44 can be rotatably mounted to the structure 42, respectively. Each arm 44 can include the lighting housing 12 adjustably mounted thereto. One of the arms 44 can have an angle and/or length less than the other arm 44, thereby allowing the arms 44 to traverse past each other without obstruction or contact.

An additional articulating arm 46 can be rotatably mounted to the structure 42 and can be configured to support a computer system 50 configured to provide control for the light systems 12. The computer system 50 can be programmed to project multiple light sources for surgical site or medical procedures illumination, for human safe pathogen killing visible light, and for human safe pathogen killing ultraviolet light. The additional arm 46 can include a conduit for wiring and computer controls. The light housing 12 and/or computer system 50 may also have a Bluetooth or wireless module 54 for connecting to the computer system 50 to a surgical site infection lighting management system and/or the pathogen killing electromagnetic radiation sources and the lights for illumination 18, 20, 22, the laser 36 and camera 37.

Figure 4:
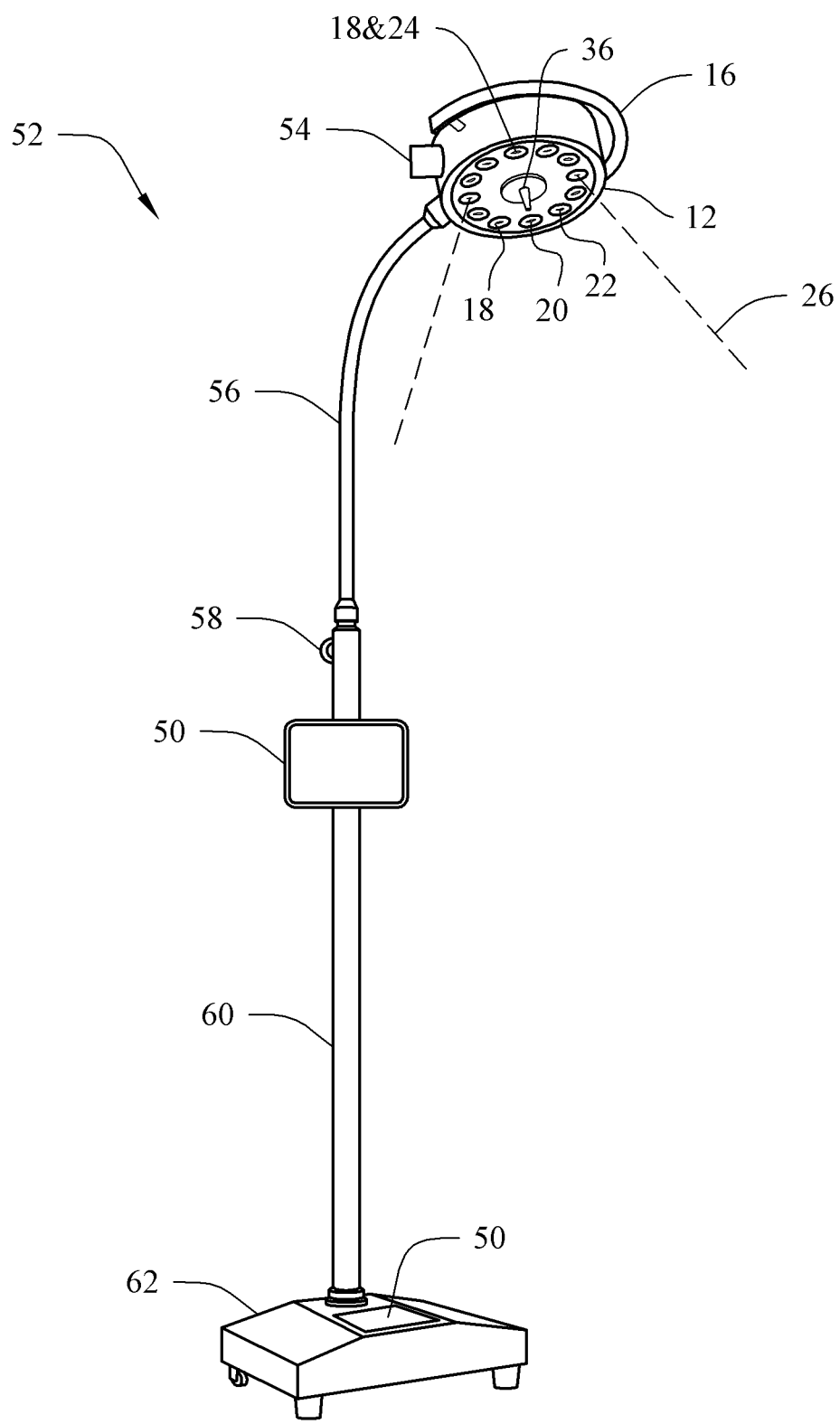
FIG. 4 is a perspective view of the floor mounted embodiment of the present technology.

Referring to FIG. 4, a portable floor supported system 52 of the present technology can be utilized. The portable floor stand or tabletop programmable lighting fixture 52 can provide a myriad of visible and ultraviolet wavelengths or bandwidths provide illumination for surgical procedures, or examinations and wound care that uses safe bactericidal, germicidal, and antimicrobial radiation. The portable floor supported system 52 can be adjusted to provide multiple sources of visible and ultraviolet light sources that produce illumination, bactericidal, germicidal, and antimicrobial radiation benefits where each of the various light and radiation sources are controlled and or programmed separately to provide a timed dose of a set energy level of a variable energy level. Every light in the fixture can be programmed to project a light source for surgical site or medical procedures illumination, for human safe pathogen killing visible electromagnetic radiation 18, and for human safe pathogen killing electromagnetic radiation 20.

The portable floor supported embodiment 52 can include the light housing 12 mounted to an articulating arm 56 adjustably or telescopically associated with a support arm 60, with a length or high to the articulating arm 56 being controlled by an adjustment screw 58. The support arm 60 can be mounted to a floor stand 62, which can include or support the computer system for setting lighting and radiation features of the surgical site infection lighting fixture 12. The floor stand 62 can include wheels or other mobility systems, and further include batteries to provide power to the computer system 50 and/or light fixture 12.

Figure 9:
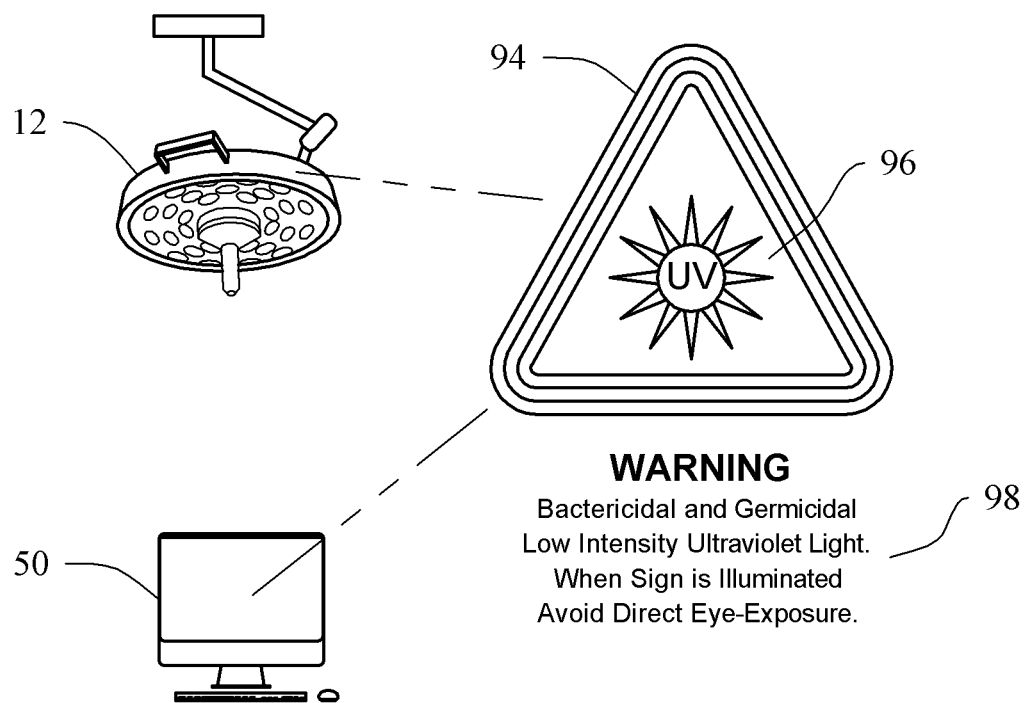
FIG. 9 is a front view of the international warning symbol for ultraviolet radiation of the present technology mounted on the medical lighting apparatus and/or the computer controlling the medical lighting apparatus.

Alternatively, the computer system can be a touch screen 50 to control the programmable features of the surgical site infection lighting fixture 12. The screen 50 can be configured to display a UV Radiation Sign and Warning Information, as best illustrated in FIG. 9, that can be illuminated during active radiation at the surgical site that requires eye protection for surgeons and medical staff.

Figure 5:
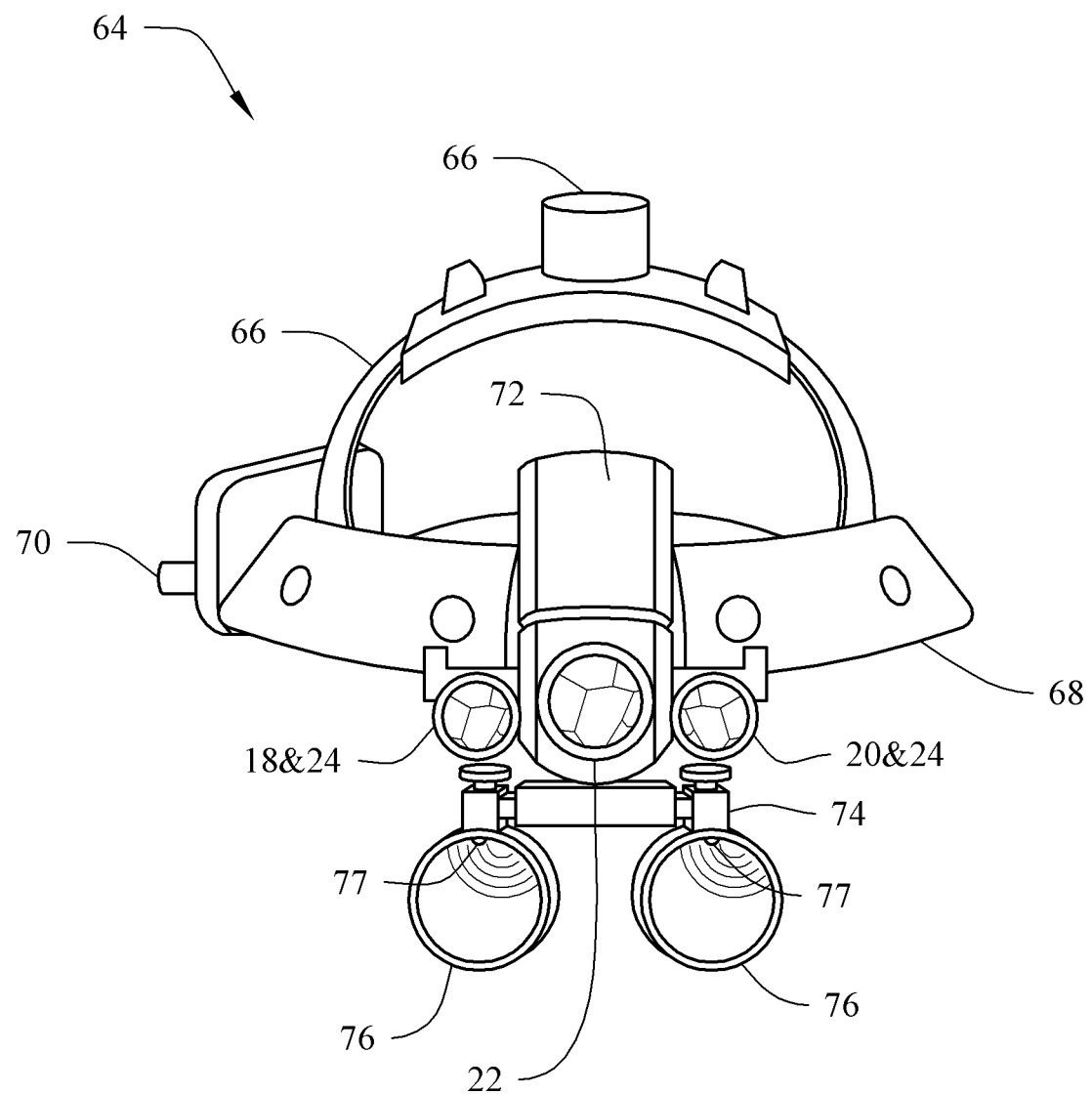
FIG. 5 is a perspective view of the head mounted embodiment of the present technology.

Referring to FIG. 5, a head mounted system 64 of the present technology can be utilized. The head mounted system 64 can include programmable lighting equipment that is worn by surgeons or medical staff that provides second electromagnetic radiation sources which have selected frequencies of 749-637 THz, 614-583 THz, and 475-384 THz 18, the first electromagnetic radiation sources have selected frequencies of 1.489-1.350 PHz, and frequencies 999-967 THz 20 for surgical procedures, or examinations and wound care that uses safe bactericidal, germicidal, and antimicrobial electromagnetic radiation. The third light source 22 provide for illuminating an area for high visibility. The head mounted system 64 are controlled and or programmed separately to provide predetermined power levels in watts or milliwatts or microwatts over a set time, which yields the effective electromagnetic radiation dose or doses from the second electromagnetic radiation 18 and/or from the first electromagnetic source 20. The head mounted system 64 can be controlled and/or programmed separately to provide pathogen killing electromagnetic doses on a fixed or variable schedule to the surgical site 4 of the patient 2.

The head mounted system 64 can include a head band and adjustment knob or system 66 configured for adjustably supporting the head mounted system 64 on a user's head. A front of the head mounted system 64 may contain rechargeable batteries 68 to supply power to the lighting system 22 and the electromagnetic radiation sources 18 and 20. The front of the head mounted system 64 can include a second electromagnetic radiation and lens combination 18, 24 on one side of a central support mount 72, the first electromagnetic radiation and lens combination 20, 24 on another side of the central support mount 72 opposite the visible light and lens combination, and the LEDs 22 mounted on the central support mount 72 between the visible lights and the electromagnetic radiation units.

A control module 70 can be included with the head mounted system 64 for receiving adjustment settings and controls from a computer system, and/or for transmitting data to the computer system. A computer can be connected to the head mounted system 64 by hardwire or by a wireless connection such as Bluetooth. Controls on the head mounted system 64 or received by the computer system can be used to manage the second electromagnetic radiation and second electromagnetic radiation units 18 & 24, 20 & 24 and bactericidal, germicidal, and antimicrobial radiation with manually controls by the surgeon or computer controlled using a wireless connection.

Binocular mounting and adjustment fixtures 74 can be mounted to the central support mount 72 below the pathogen killing electromagnetic radiation sources and the lights for illumination units 18, 20, 22. A binocular lenses 76 for magnification of the surgical site during operations can be adjustably mounted to each of the binocular fixtures 74. An indicator light 77 that is visible to the person wearing the head mounted system 64 and visible to others nearby will illuminate only as a visible indicator light during the surgical or medical procedure when pathogen killing electromagnetic radiation dose or doses are actively being delivered to the surgical or medical target area site 4 from any electromagnetic radiation source 18 and/or 20.

It can be appreciated that the laser and/or camera can be mounted to the central support mount 72. The head mounted system 64 can provide a user with the ability to aim the pathogen killing electromagnetic radiation sources and the lights for illumination 18, 20, 22 wherever the user's head is pointing. Giving increased flexibility and visibility to the user of the surgical site.

Figure 6:
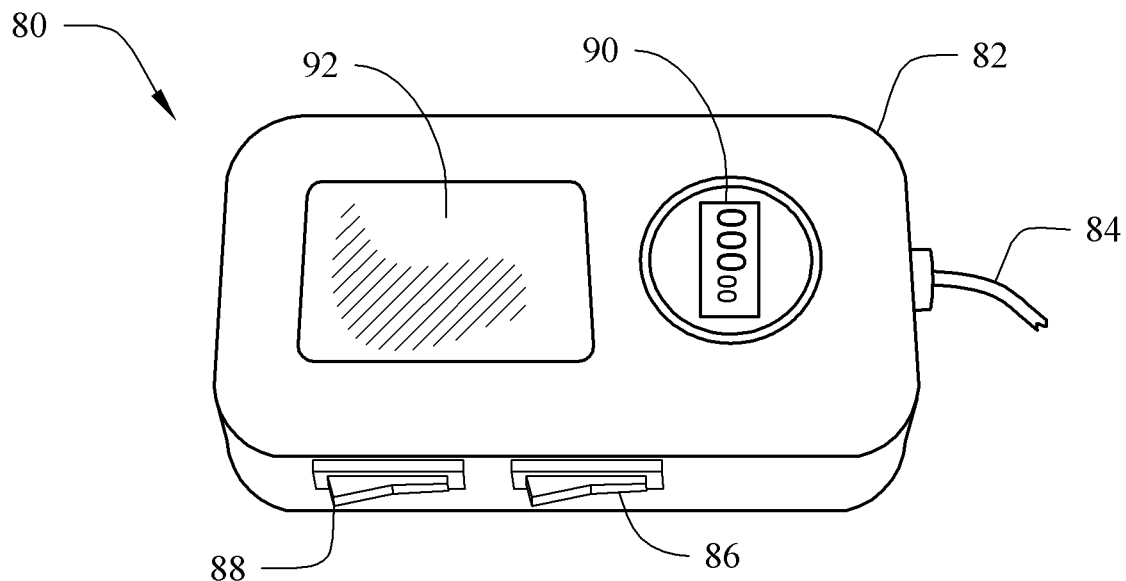
FIG. 6 is a top perspective view of the hand-held embodiment of the present technology.
Figure 7:
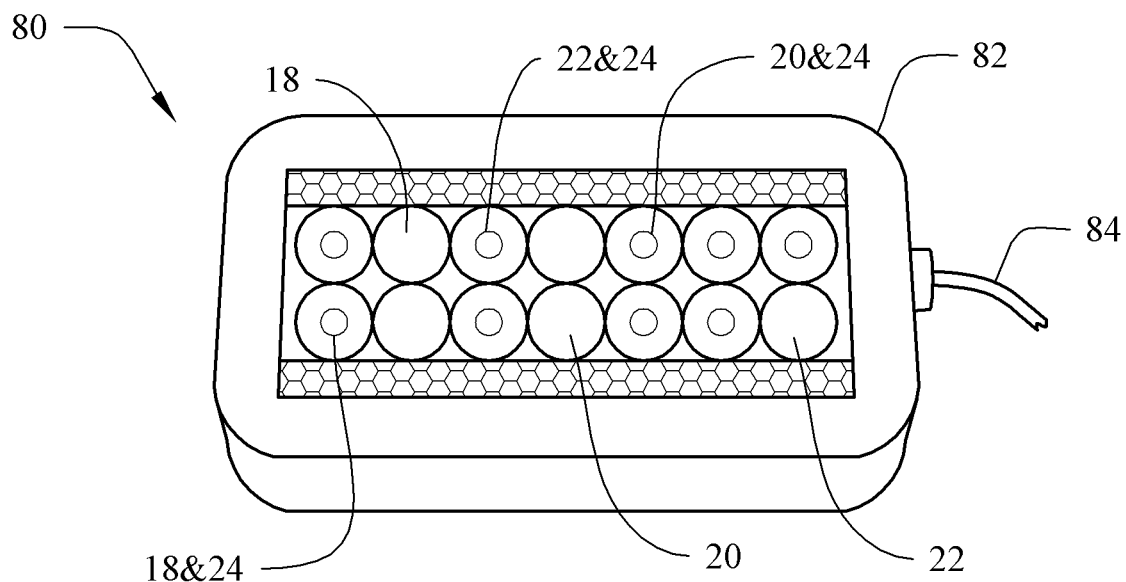
FIG. 7 is a bottom perspective view of the hand-held embodiment of the present technology.
Figure 8:
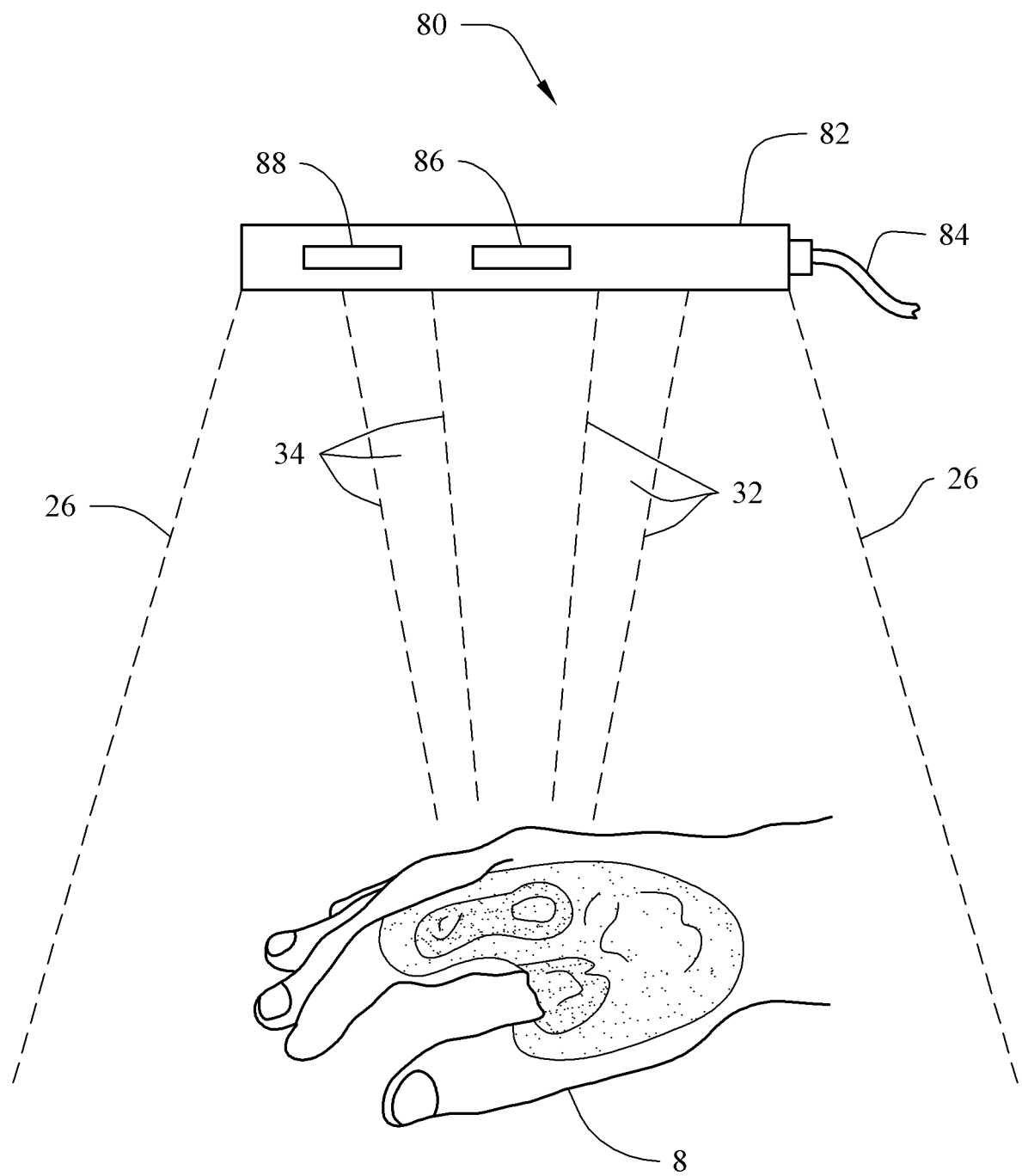
FIG. 8 is a side plane view of the hand-held embodiment of the present technology in operation treating a hand of a patient.

Referring to FIGS. 6-8, a handheld system 80 of the present technology can be utilized. The handheld system 80 can be programmable and can be used by surgeons or medical staff that provides a multiple visible and ultraviolet wavelengths or bandwidths provides illumination for surgical procedures, or examinations and wound care that uses safe bactericidal, germicidal, and antimicrobial radiation. Every light in the handheld system 80 can be programmed to project a light source for surgical site or medical procedure illumination, human safe pathogen killing visible light, and human safe pathogen killing ultraviolet light. The handheld system 80 can be adjusted to provide multiple sources of visible and ultraviolet light sources that produce illumination, bactericidal, germicidal, and antimicrobial radiation benefits where each of the various light and radiation sources can be controlled and/or programmed separately to provide a timed dose of a set energy level of a variable energy level. The handheld system 80 can be controlled and or programmed separately to provide a timed dose of a set energy level of a variable energy level deep within the surgical field.

The handheld system 80 can include a durable case 82 that houses its components. A universal serial bus (USB) port and/or cord 84 can be used to recharge onboard batteries and provide programming communication from a computer or control module to the device. It can be appreciated that any wired protocol and/or system can be utilized in place of the USB port. Further, it can be appreciated that the handheld system 80 can include a wireless communication module configured to wirelessly connect to the computer system.

A first On-Off switch 86 can be provided for controlling the safe visible light for illumination. This illumination may contain wavelengths or bandwidths of visible and ultraviolet light that provide safe bactericidal, germicidal, and antimicrobial radiation.

A second On-Off switch 88 can be provided for safe visible light and ultraviolet radiation that safe, and can be programmed separately to provide a timed dose of a set energy level of a variable energy level. The handheld system 80 can be controlled and/or programmed separately to provide a timed dose of a set energy level of a variable energy level deep within the surgical field.

As best illustrated in FIG. 7, the handheld system 80 can include second electromagnetic radiation and first electromagnetic radiation units 18, 20 can be configured to provide bactericidal, germicidal, and antimicrobial radiation that is 100% safe for human exposure, including the patient and medical staff at any exposure level and amount of time. Multiple focused second electromagnetic radiation- and the lens or lenses 18&24 of varying electromagnetic radiation frequencies and illumination lighting wavelengths or bandwidths that are programmable to provide bactericidal, germicidal, and antimicrobial radiation benefits where the exposure level and amount of time are engineered to be safe for humans. These beams of light may be manually turned on and off or programmed to turn on and off multiple times during an operation or medical procedure. Multiple focused first electromagnetic radiation frequencies 20&24 of varying frequencies, wavelengths or bandwidths can be programmable to provide bactericidal, germicidal, and antimicrobial radiation benefits where the exposure level and amount of time are engineered to be safe for humans. These beams of the second and the first electromagnetic radiation may be turned on and off multiple times during an operation or medical procedure.

Multiple LEDs 22 can be included to provide high visibility for surgeons and medical staff during an operation or medical procedure. It can be appreciated that the second and the first electromagnetic radiation 18, 20, the focused second electromagnetic radiation—18&24, the first electromagnetic radiation 20&24, and the LEDs 22 can be arranged on the bottom side of the handheld system 80 in any arrangement, pattern and/or array.

The handheld system 80 can further include a control setting and stopwatch unit 90 that can be used to manage the handheld system 80. A computer can be connected to the handheld system 80 apparatus by hardwire or by a wireless connection such as Bluetooth. Controls on the handheld system 80 can be used to manage the visible and ultraviolet and bactericidal, germicidal, and antimicrobial electromagnetic radiation manually by the surgeon or medical staff can be set and managed by the computer using a wireless connection. The timing feature can include audible settings to alert the user when certain ultraviolet radiation is in use.

A touch control screen 92 can be utilized to manage and display use functions in real time. The touch screen 92 can be further utilized to control the programmable features of the handheld system 80. The screen 92 can display the UV Radiation Sign and Warning Information that is illuminated during active radiation at the surgical site that requires eye protection for surgeons and medical staff.

Referring to FIG. 8, an exemplary use of the handheld system 80 can include positioning the body 82 above a surgical site, for example a hand 8 of a patient. The effective limits of all light and radiation illumination area 26 can be adjusted by raising and/or lowering the body 82. The electromagnetic radiation can be focused to a concentration area 32, 34 on a specific site on the hand 8. This can be accomplished by adjusting the silica lens 24 associated with any combination of the visible lights 18 and electromagnetic radiation units 20. The concentration area 32 can also be adjusted by raising and/or lowering the body 82.

Referring to FIG. 9, an international warning symbol 94 for ultraviolet-radiation can be mounted and/or displayed on the light system 12 and/or computer 50. A central region 96 of the sign can illuminate and can have an audible signal during active electromagnetic radiation that alerts patients and medical providers the personal protection equipment is required for control and management for human protection during any active use of any potential harmful ultraviolet lighting. Written information 98 for safe use of a surgical site infection lighting management system can further be provided and/or displayed.

Figure 10:
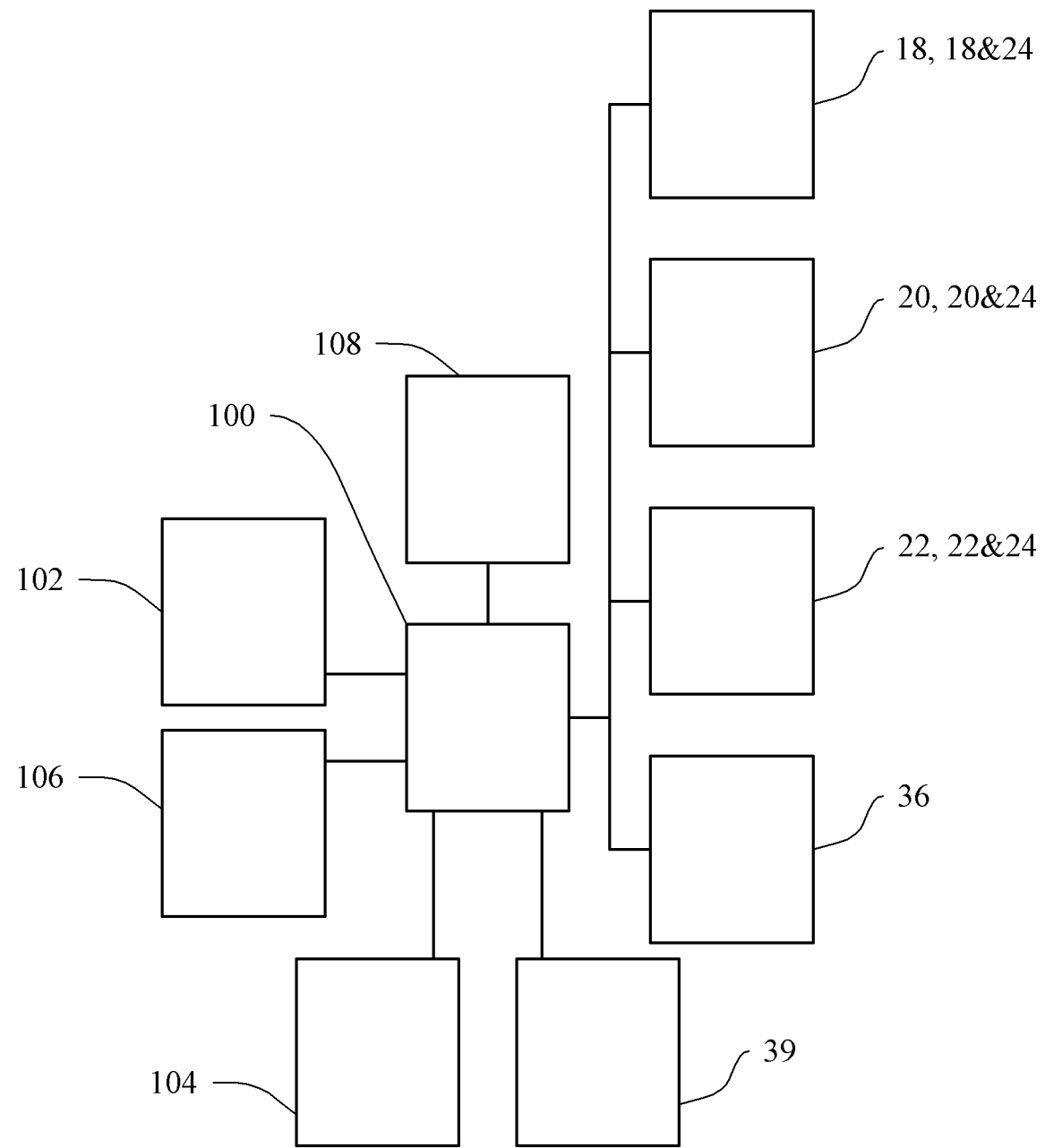
FIG. 10 is a block diagram of components utilizable with the medical lighting apparatus, system, method and controls of the present technology.

As best illustrated in FIG. 10, the computer system 50 associated in or with the present technology can include an electronic or computer system including a processor or processing unit 100, a user interface associated with the processing unit, a storage or memory unit 102, a display unit 104, a communication module 106 and/or a motion sensor 108. At least one RAM memory and/or at least one non-volatile long-term memory can be operably connected or connectable with the processing unit 100. The second electromagnetic radiation 18, 18 & 24, the first electromagnetic radiation units 20, 20 & 24, the high illumination lighting LEDs 22, 22 & 24, the laser 36, the camera 37 and the symbol 94 can all be in operable communication with the processing unit 100, the memory unit 102 and/or the display unit 104. It can be appreciated that the camera 37 can be any device capable of capturing images and/or video, and can be associated or integrated with a microphone.

Unit 100 is the computer module that can be programmed for a specific surgical or medical procedure to set the system for human safe dosing for the pathogen killing radiation from the second electromagnetic radiation—18 and the radiation from the first electromagnetic radiation 20. The computer module (unit 100) controls the scheduled dose setting controls for the ultraviolet or visible light frequency, energy levels, and scheduled time exposure length of electromagnetic radiation deliver schedule during the surgical or medical procedure for the patient exposure to the second electromagnetic radiation 18 and the first electromagnetic radiation 20. The use of the pathogen killing second and first electromagnetic radiation 18 and 20 may be used for pre-operative, intra-operative and/or post-operative dosing. The computer module also controls the high visible LED light 22 intensity and character that is used for illumination of the surgical or medical procedure site for optimum visibility during the procedure. The focus of the pathogen killing electromagnetic radiation sources and the lights for illumination 18, 20, and 22 can be managed by computer programming of unit 100 for the lens 24 automated adjustment. The lens 24 can also be manually adjusted as well. The adjustment to the lens 24 that sets the diameter or shape of the light that is projected onto the surgical site 4 in combination with the power of the pathogen killing lights 18 and 20 ensures that the dose in energy (typically in milli joules) efficiently kills the pathogen population in a minimal time, while being safe to the patient 2. The computer 100 setting can be pre-programmed and/or adjusted in real-time to ensure flexibility in use and efficiencies.

It can be appreciated that any embodiment of the present technology can be configured or configurable as a complete system including the computer system. Alternatively, it can be appreciated that the second electromagnetic radiation—18, 18&24, the first electromagnetic radiation units 20, 20&24, the LEDs 22, 22&24, the laser 36, and/or the camera 37 can be provided as modules that are connectable and/or interchangeable with the present technology system. Even further in the alternative, the present technology can include software or programming code as part of an operating system or application running on or controlling the any component associated with the present technology.

The present technology can be associated or integrated with, but not limited to, smart phones, smart watches, tablets, notebooks, desktop computers, laptops, digital cameras (point and shoot, single-lens reflex, video cameras, high end audio/visual gear), eyewear, drones, gimbals and other stabilizers, handheld units, mountable units, wearables, "Internet of Things" (IoT), and the like.

The processing unit 100 can be configured or configurable to receive an input by a user or by preset parameters or by sensors applying input data, such as but not limited to, distance values received by the laser 36.

In various example embodiments, the present technology can operate as a standalone device or may be connected (e.g., networked) to other devices. In a networked deployment, the electronic device may operate in the capacity of a server or a client machine in a server-client network environment, or as a peer machine in a peer-to-peer (or distributed) network environment. The electronic device may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that device. Further, while only a single electronic device is illustrated, the term "device" shall also be taken to include any collection of devices that individually or jointly execute a set (or multiple sets) of instructions to perform any one or more of the methodologies discussed herein.

The example computer system includes a processor or multiple processors (e.g., CPU, GPU, or both), and a main memory and/or static memory, which communicate with each other via a bus. In other embodiments, the computer system may further include a video display (e.g., a liquid crystal display (LCD)). The computer system may also include an alpha-numeric input device(s) (e.g., a keyboard), a cursor control device (e.g., a mouse), a voice recognition or biometric verification unit (not shown), a drive unit (also referred to as disk drive unit), a signal generation device (e.g., a speaker), a universal serial bus (USB) and/or other peripheral connection, and a network interface device. In other embodiments, the computer system may further include a data encryption module (not shown) to encrypt data.

The present technology can be a module operably associated with a drive unit, with the drive unit including a computer or machine-readable medium on which is stored one or more sets of instructions and data structures (e.g., instructions) embodying or utilizing any one or more of the methodologies or functions described herein. The instructions may also reside, completely or at least partially, within the memory and/or within the processors during execution thereof by the present technology can. The memory and the processors may also constitute machine-readable media.

The instructions may further be transmitted or received over a network via the network interface device utilizing any one of a number of well-known transfer protocols (e.g., Extensible Markup Language (XML)). While the machine-readable medium is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the device and that causes the device to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

It should be understood that the particular order in which the operations in the figures have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods and/or processes described herein are also applicable in an analogous manner to the method described above with respect to the figures.

For situations in which the systems, interfaces and/or methods discussed above collect information about users, the users may be provided with an opportunity to opt in/out of programs or features that may collect personal information (e.g., information about a medical history, biometric data, and environmental data such as location). In addition, in some or all implementations, certain data may be anonymized in one or more ways before it is stored or used, so that personally identifiable information is removed. For example, a user's identity may be made anonymous so that the personally identifiable information cannot be determined for or associated with the user, and so that user preferences or user interactions are generalized (for example, generalized based on user demographics) rather than associated with a particular user. Data encryption can also be utilized and "tokenized" access using the blockchain technology can also be utilized to further obfuscate the user's identity.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, middleware, software, applications in programming interface (API's) or any combination thereof.

Some aspects of the present technology can include apparatus, methods, and controls that can be used as surgical or medical procedure lighting that provides illumination with the use of multiple LED or halogen bulbs or other safe and bright lighting sources across the entire ultraviolet spectrum and visible light spectrum. The light system can provide illumination for surgical or medical procedures and also provided pathogen killing benefits when the electromagnetic radiation is delivered using a fixed or adjustable focused beam and energy levels of the managed dose or doses of bactericidal, germicidal, and antimicrobial radiation during a medical or surgical procedure. The present technology can be programmed to project a light source for surgical site or medical procedures illumination, human safe pathogen killing electromagnetic radiation. The pathogen killing radiation can include the first electromagnetic radiation frequencies of 1.489-1.350 PHz, and frequencies 999-967 THz and the second electromagnetic radiation frequencies of 749-637 THz, 614-583 THz, and 475-384 THz; all within the suite of lights and electromagnetic radiation that are used in the present technology; or select sets of electromagnetic radiation frequencies may be chosen to meet surgical and pathogen killing objectives. The pathogen killing electromagnetic radiation utilized in the present technology is safe for human and animal use and can be programmed by a computer or manually controlled by a technician where the surgical site infection management lighting system uses one or more visible and safe colored laser beam(s) so that the operator can visually adjust the focused radiation sources to be aimed at a surgical or medical site during the surgical or medical procedure and can also be used in veterinary medicine.

Some aspects of the present technology can include be used in a surgical procedure or post-operative care where the objective is to kill bacteria, viruses and other harmful pathogens, such as fungus, protozoa, yeast, et cetera, where a certain suite of pathogens that are targeted to be killed and destroyed by a scheduled dose of electromagnetic-radiation with a fixed frequency or frequencies. The doses of electromagnetic radiation are harmless to patients and medical providers and the following example provides one type of use of the invention. A hypothetical scenario for use of the present technology can be a patient undergoes a laparotomy surgical procedure where the surgical incision on the patient is 12 centimeters long and two additional centimeters are added to give sterilization margins. Beams of pathogen killing electromagnetic radiation will be focused to have a 14-centimeter diameter, with an area of 154 square centimeters where the focal length and energy level of each of the selected electromagnetic radiation are projected from a ceiling or wall mounted lighting system that may be 180 centimeters above the surgical site. The beam or beams of electromagnetic radiation will be limited to the precise area of the surgical site, and will only be projected on a scheduled basis to meet objectives destroying pathogens and thereby reducing or eliminating potential surgical site infection. Engineering and design practices will be used to ensure that the proper dose of electromagnetic radiation is projected to the surgical site.

The present technology can be used to kill 99% of pathogens known to be destroyed with electromagnetic radiation frequencies of 1.489-1.350 PHz with no adverse effects on human skin or the human eye and could be used to achieve the objectives of the present technology. The ultraviolet light dosing would be dependent on the actual time of the medical procedure, where the actual surgical procedure dose could be one 12.5 seconds each and would provide a 10 millijoule dose. Several doses over the length of the surgical procedure at the same level may be used during the medical procedure. A post-operative dose could be delivered as a final closing step. All electromagnetic radiation doses will be configured to be safe and harmless to the patient. This electromagnetic radiation at the prescribed energy level and time will typically kill around 30 harmful pathogens. Table 1 below shows a hypothetical scheduled for the use of frequencies 1.489-1.350 PHz for pathogen destruction.

human use because the radiation frequency range of 1.498 and 1.350 PHz is known to be harmless for human use in low doses. The total electromagnetic radiation frequency range of 1.498 and 1.350 PHz will be 800 microwatts multiplied by 15 seconds, which provides an engineered factor of safety of about 1.2 and will deliver 12,000 microjoules or 12.0 millijoules per square centimeter of pathogen killing radiation. Each of the five doses will kill 99% of the targeted pathogens each time and will be safe for human exposure. Electrical engineering, mechanical engineering, biomedical engineering, and computer programming is utilized to ensure the correct energy level and dose time are designed and delivered to the surgical site for optimal patient health and healing. Other scheduled doses of several different electromagnetic radiation frequencies of bactericidal and pathogen killing electromagnetic radiation would be engineered and used during the surgical procedure. Possibly electromagnetic radiation in the spectral range of Blue Light with frequency range of 749 to 637 THz is known to kill at least 26 known pathogens such as gram-positive *Streptococcus* thermophiles and methicillin resistant *Staphylococcus aureus* (MRSA), could be added to the suite electromagnetic radiation as well.

Another electromagnetic radiation could be a krypton-chlorine (Kr—Cl) excimer lamp that produces a frequency 1.350 PHz with a bandpass filter could be used to remove the lower- and higher-wavelength components. The electromagnetic radiation dose is engineered and designed for the use of a predetermined power at a set exposure time for the radiation of a specific patient target site to provide effective pathogen destruction and to ensure patient safety. Patients benefit from the use of an electromagnetic radiation frequency of 1.350 PHz which kills MRSA and a myriad of other harmful pathogens efficiently. The benefit to the patient for used of frequency 1.350 PHz in the frequency range between 1.489 and 1.350 PHz is that the frequency 1.350 Phz kills bacteria efficiently regardless of their drug-resistant proficiency, but without the skin damaging effects associated with conventional germicidal electromagnetic radiation exposure that are used to kill pathogens in non-human exposure application.

TABLE 1

Electromagnetic radiation for pathogen destruction using the frequency range between 1.498 and 1.350 petahertz

| Phase of procedure | Scheduled radiation | Radiation power: per sec. in microwatts | Radiation time in sec. | Lethal dose for a select set of 30 pathogens is 10 mj per cm$^2$ |
|---|---|---|---|---|
| Pre-incision 0 to 20 minutes | at 18 min. | 800 | 12.5 | 10,000 = microjoules = 10 millijoules per cm$^2$ |
| Intra-operative 21 to 120 minutes | at 25 min | 800 | 12.5 | 10,000 microjoules = 10 millijoules per cm$^2$ |
| | at 60 min. | 800 | 12.5 | 10,000 = microjoules = 10 millijoules per cm$^2$ |
| | at 115 min. | 800 | 12.5 | 10,000 = microjoules = 10 millijoules per cm$^2$ |
| Closure of incision 121 to 140 minutes | at 130 min. | 800 | 12.5 | 10,000 microjoules = 10 millijoules per cm$^2$ |

During the surgical procedure electromagnetic radiation frequencies in the range of 1.498 and 1.350 PHz can be used with 800 microwatts power for 15 seconds delivered to the surgical site that will provide sufficient pathogen destruction. Using an extra 2.5 seconds of time, i.e. 15 seconds rather than 12.5 seconds, ensures complete pathogen destruction at the surgical site, while still being safe for One of the other electromagnetic radiations with a frequency 1.448 PHz also effectively kills methicillin-resistant *S. aureus* (MRSA) bacteria and the radiation has insignificant impacts to human skin because frequencies around 1.448 PHz and energy levels used to kill pathogens do not penetrate into human skin and any minor penetration is attenuated without impact to human cell nuclei.

Some aspects of the present technology can include apparatus, methods, controls, and systems used in a surgical procedure or postoperative care where the objective is to kill and destroy bacteria, viruses and other harmful pathogens, such as fungus, protozoa, yeast, et cetera, where a certain suite of pathogens that are targeted to be killed and destroyed by a scheduled dose of electromagnetic radiation with a fixed frequency. The present technology could use continuous illumination with blue light in the spectral range of 749-599 THz that is known to kill harmful pathogens. Electromagnetic radiation frequencies in the range of 1.489-1.350 PHz as engineered and deployed are efficient and effective for pathogen destruction and will not have adverse effects on human health. The present technology may be programmed to leave one or several electromagnetic radiation frequencies turned on continuously during the surgical or medical procedure, where the surgical site infection management system computer will be used to control and to adjust the focus and dose of the pathogen killing electromagnetic radiation.

Some aspects of the present technology can include apparatus, methods, controls, and systems used as a special treatment for burn victims a surgical where frequency 1.448 PHz to 1.350 PHz and other electromagnetic radiation pathogen killing frequencies in several ranges can be used to treat large areas of the burn victims body during initial care and throughout post patient care to reduce or eliminate infection that adversely impacts or kills the patient. The present technology can be configured to kill and destroy bacteria, viruses and other harmful pathogens, such as fungus, protozoa, yeast, et cetera, where a certain suite of pathogens that are targeted to be killed and destroyed by scheduled doses of electromagnetic radiation with managed frequencies and energy levels that have been shown to have no impact on the human body or eyes. All engineered and deployed electromagnetic radiation doses can be configured to be safe and harmless to the patient and medical providers, and the radiation sources such as Blue Light can be turned on continuously during the surgical or medical procedure or during post-operative patient care.

Some aspects of the present technology can include apparatus, methods, controls, and systems that can use special focusing lenses for overhead lighting or for a surgical headlamp that are made from fused silica and that projects the visible and electromagnetic radiation to a specific area and allows targeted pathogen killing radiation to be focused on the patients surgical site during surgical or medical procedures. The fused silica lenses can be part of the present technology and the focus can be set manually or by the computer programming features to project the pathogen killing electromagnetic radiation onto the surgical site or patient care surface. An example of the application of the fused silica focusing capabilities could be: the lighting system can be 180 centimeters above the patient's surgical site, and the fused silica lenses can be focused to deliver a scheduled pathogen killing electromagnetic radiation dose to the surgical site that would be 25 centimeters in diameter. This can allow the health benefits of infection reduction or elimination at the surgical site, while limiting radiation exposure to focus area only.

A visible laser unit can be included to show the center of the safe pathogen killing electromagnetic radiation which is not visible, and the laser unit can have the capability of measuring the precise distance between the lighting and the surgical site and can be used as part of the control systems to set the configured energy level and time of the radiation dose. Within the center of the electromagnetic radiation system there can be a camera with adjustable lens for magnification to observe a surgical or medical procedure in real time and can be used to record the procedure for later viewing.

Some aspects of the present technology can include a mobile electromagnetic radiation in a range between frequencies 1.489-1.350 PHz that is used during human surgical or dental procedures to kill bacteria, viruses, and other pathogens in real time during a surgical procedure that is in progress. The mobile system can be used in combination with a conventional illumination lighting systems and units that are currently used in the medical industry and practice by adding the apparatus and controls to deliver human safe electromagnetic radiation in doses that will be safe and useful for the patient and medical providers that are performing the surgical or dental procedure. The energy level of the electromagnetic radiation in millijoules may be adjusted for the time of the procedure to optimize the pathogen killing medical benefits, and are capable of being customized for continuous use on burn patients, critical care patients who are at risk of airborne pathogen infection, and for newborn humans where the mobile device has both a power cord and rechargeable batteries as a power sources.

Some aspects of the present technology can include apparatus, methods and controls that are used as pathogen killing electromagnetic radiation system to pre-treat surface area of human tissues or organs prior to transplant surgical procedures to safely kill pathogens that may exist on the organ after harvest and prior to transplantation, or pre-treat any synthetic manufactured device including metals, polymers, and ceramics, prior to placement in the human body that will be implanted. In addition, the lighting system can have a high utility for use to pre-treat biologic therapies, such as stem cells or platelet rich plasma, prior to placement in the human body.

Some aspects of the present technology can include a method, apparatus, and system that can be contained within or integrated with a headlamp worn by the surgical staff, to deliver illumination for surgical procedures and focused pathogen killing electromagnetic radiation on the surgical site during the surgical procedure. The headlamp can include three light emitting diodes: a first for the emission of the pathogen killing electromagnetic radiation with frequencies 1.489-1.350 PHz and/or 999-967 THz, a second electromagnetic radiation with frequencies of 749-637, 614-583 and 475-384 THz, and a third for emission of visible high quality light for illumination of the surgical or medical procedure site. The pathogen killing electromagnetic radiation can be programmed for a specific dose of radiation frequencies and energy levels. The headlamp can have control setting that allow the user to manage the features of the device, where the controls can be manually set while wearing the device or can be set remotely by wired or wireless computer programming prior to a surgical procedure. The headlamp can include binoculars for magnification of the surgical site area and the lenses are made from glass or polycarbonate material to ensure that the electromagnetic radiation is filtered out by the lenses in the binoculars are coated with materials that protect the human eye from any and all electromagnetic radiation.

Some aspects of the present technology can include a method, apparatus, and system that uses a tabletop lamp or floor portable lamp to deliver focused pathogen killing electromagnetic radiation—that is focused on or within the surgical or medical procedures site during the procedure and for daily scheduled use of ongoing patient care during wound dressing, and procedures such central line insertions, and site sterilization to reduce or eliminate infections while the patient heals.

Some aspects of the present technology can include apparatus and methods that can use segments from the visible and ultraviolet-spectrum of solar radiation, that provides illumination for surgical procedures that is managed by a computer-controlled method, apparatus and system to provide safe and effective health benefits for humans and other applications. The present technology may include use without human exposure for bactericidal, germicidal, virus and parasite destruction and includes a motion detection sensor 108, as best illustrated in FIG. 10, will allow the system to shut off or reduce the light and electromagnetic radiation for safe and beneficial human exposures of the various frequencies. The present technology can use a time cycled set for on and off activity for each of the separate electromagnetic radiation frequency or frequencies for optimal and safe human exposures. The present technology can revert to a full-strength electromagnetic radiation after all humans have vacated the area.

Some aspects of the present technology can include apparatus, methods, controls, and systems that can be utilized within a handheld computer programmable mobile device to be utilized in the wound care setting to eliminate primary and decrease secondary infections in open wounds, during pre-operative, intra-operative, or post-operative procedures.

Some aspects of the present technology can include apparatus, methods, controls, and systems that can include an international warning symbol for ultraviolet radiation mounted on the lighting system and illuminates during active radiation that requires controls and management for human protection and includes written information for safe use of the present technology. Where the signage can be controlled by hardwire or wireless connection to the lighting system, and where the radiation warning sign illumination and audible signals can provide patients and medical providers with information regarding the hazardous of the radiation, and allows humans to use personal protection equipment, including eyewear with ultraviolet filtering lenses that filters out the electromagnetic radiation frequencies.

While embodiments of the medical lighting and electromagnetic radiation apparatus, system, method and controls have been described in detail, it should be apparent that modifications and variations thereto are possible, all of which fall within the true spirit and scope of the present technology. With respect to the above description then, it is to be realized that the optimum dimensional relationships for the parts of the present technology, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present technology. For example, any suitable sturdy material may be used instead of the above-described. And although managing or killing airborne or surface pathogens or diseases in medical use during surgery or dental procedure have been described, it should be appreciated that the present technology herein described is also suitable for killing pathogens located on any surface or in a room.

Therefore, the foregoing is considered as illustrative only of the principles of the present technology. Further, since numerous modifications and changes will readily occur to those skilled in the art, it is not desired to limit the present technology to the exact construction and operation shown and described, and accordingly, all suitable modifications and equivalents may be resorted to, falling within the scope of the present technology.

What is claimed as being new and desired to be protected by Letters Patent of the United States is as follows:

1. An electromagnetic radiation system for providing bactericidal, germicidal, antimicrobial and/or pathogen killing effects to a target site of a patient using electromagnetic radiation and visible light sources during a time period associated with surgical or medical procedures, the electromagnetic radiation system comprising:
   a first electromagnetic radiation source configured to radiate a first electromagnetic radiation at a first electromagnetic radiation frequency selected from the group consisting of 1.489-1.350 petahertz (PHz), and 999-967 terahertz (THz), the first electromagnetic radiation source being a plurality of first electromagnetic radiation sources;
   a second electromagnetic radiation source configured to radiate a second electromagnetic radiation at a second electromagnetic radiation frequency selected from the group consisting of 749-637 THz, 614-583 THz, and 475-384 THz that have pathogen destruction capabilities at engineered and administered energy dose levels;
   a third light source configured to radiate visible light at a wavelength, bandwidth or frequency different than of the first electromagnetic radiation and the second electromagnetic radiation, where the function of the third light source is for illumination and high visibility which provides the surgeon and medical staff optimal vision while performing a surgical or medical procedure; and
   a computer system in operable communication with the first electromagnetic radiation sources, the second electromagnetic radiation source, the third light source, the computer system being configured or configurable to control any one or any combination of the first electromagnetic radiation source, the second electromagnetic radiation source and the third light source;
   wherein the first and second electromagnetic radiation frequencies are configured or configurable to deliver human safe electromagnetic radiation at an energy level and dose time to the target site on a patient that is effective in destroying harmful pathogens in real time as the surgery or medical procedure is in progress and thereby reducing or eliminating surgical or postoperative infections;
   wherein an energy level of the first electromagnetic radiation and the second electromagnetic radiation at a predetermined power level in watts or milliwatts or microwatts multiplied by the time in seconds, which yields the effective electromagnetic radiation dose, which is the energy level in joules, millijoules or microjoules, and the electromagnetic radiation dose being configured or configurable for delivery to each square centimeter of the target site on the patient, and electromagnetic radiation doses are scheduled for and delivered to the surgical or medical procedure site one or multiple times during the surgery or medical procedure;
   wherein the first electromagnetic radiation sources in the frequency range of 1.489-1.350 PHz are activated and configured at the power level of 800 microwatts and the dose time of 12.5 seconds that results in a dose of 10 millijoules that is delivered to the target site one or multiple times during the surgical or medical procedure to achieve human safe pathogen destruction and to not damage or kill human cells;

wherein the 1.489-1.350 petahertz electromagnetic radiation at the effective dose energy of 10 millijoules is configured to destroy and kill fragile microorganisms that are 10 to 100 times smaller than human cells, and wherein the first and second electromagnetic radiation are configured to not penetrate, affect, damage or kill the human cells because of the size of the human cells are one to two magnitudes larger than the microorganisms.

2. The electromagnetic radiation system according to claim 1, wherein one or more of the first electromagnetic radiation sources including a focusable lens and one or more not including the focusable lens, wherein the second electromagnetic radiation source is a plurality of second electromagnetic radiation sources with one or more of the second electromagnetic radiation sources including the focusable lens and one or more of the second electromagnetic radiation sources not including the focusable lens, and wherein the third light source is configured or configurable to provide illumination for visibility of the target site.

3. The electromagnetic radiation system according to claim 1 further comprises a laser unit located centrally within an array of the first electromagnetic radiation sources, the second electromagnetic radiation source and the third light source each being radially arranged about the laser unit, wherein the laser unit is configured to radiate laser light toward an illumination area illuminated by the first electromagnetic radiation sources, the second electromagnetic radiation source.

4. The electromagnetic radiation system according to claim 1 further comprises a distance sensor configured to sense reflected laser light utilizable in determining a distance of the first electromagnetic radiation sources, the second electromagnetic radiation source and the third light source to the target site, where the distance between the pathogen killing electromagnetic radiation sources in the electromagnetic radiation system and the patient's surgical site is used to focus area of radiation or illumination and allows for computer controlled adjustment of the electromagnetic radiation system, and is used in setting the distribution of the electromagnetic radiation frequency, or frequency ranges, at predetermined power level over a set time, which yields the effective electromagnetic radiation dose, where electromagnetic radiation frequency at a certain minimum energy level in joules, millijoules or microjoules results in the pathogen destruction, thereby achieving the reduction or elimination of site specific infections at the target surgical or medical procedures site on the patient, while being safe to human cells and the patient.

5. The electromagnetic radiation system according to claim 1 further comprises a camera configured to capture an image or video of at least the target site.

6. The electromagnetic radiation system according to claim 1 further comprises a motion sensor configured to detect motion in an area above the target site or adjacent the first electromagnetic radiation sources, the second electromagnetic radiation source.

7. The electromagnetic radiation system according to claim 1 further comprises a laser unit, a distance sensor, a camera, and a motion sensor, wherein the computer system is configured or configurable to control any one or any combination of the first electromagnetic radiation sources, the second electromagnetic radiation source and the third light source based on signals received from the distance sensor and the motion sensor, and wherein the first electromagnetic radiation sources, the second electromagnetic radiation source and the third light source being a radially arranged about the laser unit centrally located therein.

8. The electromagnetic radiation system according to claim 1, wherein the first electromagnetic radiation sources, the second electromagnetic radiation source and the third light source are integrated in a body.

9. The electromagnetic radiation system according to claim 1, wherein the electromagnetic radiation system is attachable to a device selected from the group consisting of an articulable arm, a floor stand, and a mobile base.

10. The electromagnetic radiation system according to claim 1 further comprises a signage configured to illuminate when any one or any combination of the first electromagnetic radiation sources and the second electromagnetic radiation source are actively delivering radiation doses.

11. The electromagnetic radiation system according to claim 1, wherein one or more of the first electromagnetic radiation sources are configured to radiate in a frequency range of 999-967 THz, where a predetermined dose of electromagnetic radiation range is a synthetic equivalent to portions of ultraviolet-B sunlight such that skin of the patient will synthesize vitamin D and D3 to promote biologic healing at the target site, where the frequency range is programmed and controlled by the computer system for safe and healing benefits, and wherein the computer system is configured to control the first electromagnetic radiation sources to administer the predetermined dose to the target site during final stages of the surgery or medical procedure.

12. The electromagnetic radiation system according to claim 1, wherein the first electromagnetic radiation sources and the second electromagnetic radiation source are configured or configurable to radiate the first electromagnetic radiation and the second electromagnetic radiation, respectively, to an area larger than a largest width of the target site, where programmable controls for electromagnetic radiation beam or beams for the first and the second electromagnetic radiations system can be set or adjusted to focus the size, shape and dimensions of the electromagnetic radiation, which will typically be larger than the target site, which is the active surgical or medical procedure site on the patient.

13. The electromagnetic radiation system according to claim 1, wherein the first electromagnetic radiation frequency and the energy level thereof are configured to provide a radiation level sufficient to kill a set of selected pathogens and to be harmless to the patient.

14. The electromagnetic radiation and visible system according to claim 1, wherein the computer system is configured to control the first electromagnetic radiation sources and the second electromagnetic radiation source to administer several doses of electromagnetic radiation to the target site during the time period of the surgery or medical procedure, including a preoperative dose, one or multiple intraoperative doses and a postoperative dose where each dose destroys or kills 99% of microorganisms and infection causing pathogens which eliminates or reduces surgical or medical infections in postoperative patient care.

15. A method of using an electromagnetic radiation system for providing bactericidal, germicidal, antimicrobial and/or pathogen killing effects to a target site of a patient or animal care, the method comprising the steps of:
   a) providing an electromagnetic radiation system deployable using an attachable device selected from the group consisting of an articulable arm, a floor stand, and a mobile base the electromagnetic radiation system comprising:

a first electromagnetic radiation source configured to radiate a first electromagnetic radiation at a frequency selected from the group consisting of 1.489-1.350 petahertz (PHz), and 999-967 terahertz (THz);

a second electromagnetic radiation source configured to radiate a second electromagnetic radiation at a frequency selected from the group consisting of 749-637 THz, 614-583 THz, and 475-384 THz; and a third light source configured to radiate visible light at a wavelength, bandwidth or frequency different to that of the second electromagnetic radiation, the third light source being configured or configurable to provide illumination for visibility of an entire surgical area of a patient;

b) illuminating the surgical area of the patient with the visible light;

c) selecting by a medical practitioner a suite of pathogens to be killed and destroyed utilizing the first and second electromagnetic radiation sources;

d) controlling the first and second electromagnetic radiation sources by way of a computer system in operable communication with the first electromagnetic radiation source and the second electromagnetic radiation source to deliver pathogen lethal doses to the target site in real time as a surgery or medical procedure is in progress, where the first electromagnetic radiation source being activated with an adjustable power level and a dose time to achieve human safe pathogen destruction;

e) administering the first electromagnetic radiation and the second electromagnetic radiation on the target site of the patient at an energy level and a dose time configured to destroy and kill microorganisms, viruses, bacteria, spores and human harmful pathogens and will not damage or kill human cells by using a frequency range of 1.489-1.350 petahertz at a power level and dose time of exposure used, and wherein the power level is 800 microwatts and wherein the dose time exposure is 12.5 seconds that results in a dose of 10 millijoules, the target site for the first and second electromagnetic radiation having a size greater than the entire surgical area; and f) providing bactericidal, germicidal, antimicrobial and/or pathogen killing effects to the target site by controlling a parameter of any one or any combination of the first electromagnetic radiation source and the second electromagnetic radiation source, wherein the parameter being selected from the group consisting of intensity, power level, electromagnetic radiation time, and a distance between the electromagnetic radiation system and the target area;

wherein the dose time of the first electromagnetic radiation at the frequency range of 999-967 THz is configured to be a synthetic equivalent to portions of ultraviolet-B sunlight such that skin of the patient will synthesize vitamin D and D3 to promote biologic healing at the target site and the dose of the first electromagnetic radiation is administered to the target site one time near an end of the surgical or medical procedure;

wherein the first electromagnetic radiation source and the second electromagnetic radiation source are configured or configurable to deliver human safe pathogen killing electromagnetic radiation at a predetermined power level in watts or milliwatts or microwatts over a set time, which yields the effective electromagnetic radiation dose, where electromagnetic radiation frequency at a certain minimum energy level in joules, millijoules or microjoules results in the pathogen destruction, thereby achieving the reduction or elimination of site specific infections at the target site on the patient in real time during surgical or medical procedures and postoperative patient recovery, and electromagnetic radiation doses are scheduled for and delivered to the surgical or medical procedure site one or multiple times during the surgery or medical procedure.

16. The method according to claim 15 further comprising the step of providing an aiming light from a laser unit positioned in a center of an array of the first electromagnetic radiation source, the second electromagnetic radiation source to visually identify the active time and location of the first and second electromagnetic radiation, and the third light source or sources that provide a high level of illumination for optimal visibility of the surgical or medical treatment site.

17. The method according to claim 15 further comprising the step of determining the distance between the electromagnetic radiation system and the target area by a distance sensor configured to sense reflected laser light emitting from a laser unit where the measured distance information is used to adjust the projected delivery of first and second electromagnetic radiation frequency or frequencies, and the energy levels, and size, dimension and shape of the electromagnetic radiation beam or beams through a lens or lenses that are part of the pathogen killing electromagnetic radiation and illumination lighting system.

18. The method according to claim 15 further comprising the step of controlling any one or any combination of the first electromagnetic radiation source and the second electromagnetic radiation source by way of the computer system in operable communication therewith and a motion sensor.

19. The method according to claim 15 further comprising the step of displaying to a display an image or video of an illumination area captured by a camera.

20. The method according to claim 15, wherein the second electromagnetic radiation source is configured to radiate at a frequency range of 749-599 THz for human safe radiation that destroys and kills pathogens.

* * * * *